(12) United States Patent
Sanchez et al.

(10) Patent No.: US 8,897,858 B2
(45) Date of Patent: *Nov. 25, 2014

(54) SYSTEM AND METHOD USEFUL FOR SARCOMERE IMAGING VIA OBJECTIVE-BASED MICROSCOPY

(75) Inventors: Gabriel Nestor Sanchez, Stanford, CA (US); Scott L. Delp, Stanford, CA (US); Mark J. Schnitzer, Palo Alto, CA (US); Michael E. Llewellyn, Palo Alto, CA (US)

(73) Assignee: The Board of Trustees of the Leland Stanford Junior Univerity, Palo Alto, CA (US)

( * ) Notice: Subject to any disclaimer, the term of this patent is extended or adjusted under 35 U.S.C. 154(b) by 42 days.

This patent is subject to a terminal disclaimer.

(21) Appl. No.: 13/305,390

(22) Filed: Nov. 28, 2011

(65) Prior Publication Data

US 2012/0143065 A1   Jun. 7, 2012

Related U.S. Application Data

(63) Continuation-in-part of application No. 12/165,977, filed on Jul. 1, 2008, now Pat. No. 8,068,899.

(60) Provisional application No. 60/947,769, filed on Jul. 3, 2007.

(51) Int. Cl.
*A61B 6/00*   (2006.01)
*A61B 5/00*   (2006.01)
*G01N 21/64*  (2006.01)
*A61B 1/04*   (2006.01)

(52) U.S. Cl.
CPC ............. *A61B 5/0062* (2013.01); *A61B 5/0086* (2013.01); *A61B 5/4519* (2013.01); *A61B 5/726* (2013.01); *A61B 5/4528* (2013.01); *G01N 21/6458* (2013.01); *A61B 5/0068* (2013.01); *A61B 5/0084* (2013.01); *A61B 5/0071* (2013.01); *A61B 5/6848* (2013.01); *A61B 5/7207* (2013.01); *A61B 1/043* (2013.01)
USPC ........................................................ 600/478

(58) Field of Classification Search
None
See application file for complete search history.

(56) References Cited

U.S. PATENT DOCUMENTS 3,655,259 A   4/1972   Miyauchi et al.
4,270,843 A   6/1981   Goto (Continued)

FOREIGN PATENT DOCUMENTS

WO   2013/082156 A1   6/2013

OTHER PUBLICATIONS

Gordon, A. M., Huxley, A. F. and Julian, F. J., "The variation in isometric tension with sarcomere length in vertebrate muscle fibres," J Physiol 184, pp. 170-192 (1966).

(Continued)

*Primary Examiner* — Michael Rozanski
*Assistant Examiner* — Lawrence Laryea
(74) *Attorney, Agent, or Firm* — Crawford Maunu PLLC

(57) ABSTRACT

Biological tissue such as skeletal and cardiac muscle can be imaged by using an objective-based probe in the tissue and scanning at a sufficiently fast rate to mitigate motion artifacts due to physiological motion. According to one example embodiment, such a probe is part of a system that is capable of reverse-direction high-resolution imaging without needing to stain or otherwise introduce a foreign element used to generate or otherwise increase the sensed light. The probe can include a light generator for generating light pulses that are directed towards structures located within the thick tissue. The system can additionally include aspects that lessen adverse image-quality degradation. Further, the system can additionally be constructed as a hand-held device.

28 Claims, 27 Drawing Sheets

(56) References Cited

U.S. PATENT DOCUMENTS

| | | | |
|---|---|---|---|
| 4,416,519 A | 11/1983 | Kobayashi | |
| 4,515,444 A | 5/1985 | Prescott et al. | |
| 4,570,641 A | 2/1986 | Lieber et al. | |
| 4,693,606 A | 9/1987 | Podolsky et al. | |
| 5,056,530 A | 10/1991 | Butler et al. | |
| 5,093,719 A | 3/1992 | Prescott | |
| 5,161,063 A | 11/1992 | Krill et al. | |
| 5,181,511 A | 1/1993 | Nickolls et al. | |
| 5,361,166 A | 11/1994 | Atkinson et al. | |
| 5,457,576 A | 10/1995 | Atkinson et al. | |
| 5,929,985 A | 7/1999 | Sandison et al. | |
| 6,198,834 B1 * | 3/2001 | Belk et al. | 382/110 |
| 6,208,886 B1 | 3/2001 | Alfano et al. | |
| 6,542,665 B2 | 4/2003 | Reed et al. | |
| 6,546,278 B2 | 4/2003 | Walsh | |
| 6,571,118 B1 | 5/2003 | Utzinger et al. | |
| 6,580,941 B2 | 6/2003 | Webb | |
| 6,639,674 B2 | 10/2003 | Sokolov et al. | |
| 6,643,071 B2 | 11/2003 | Schnitzer | |
| 6,760,112 B2 | 7/2004 | Reed et al. | |
| 6,766,184 B2 | 7/2004 | Utzinger et al. | |
| 6,785,471 B2 | 8/2004 | Lee et al. | |
| 6,795,199 B2 | 9/2004 | Suhami | |
| 6,839,483 B2 | 1/2005 | Reed et al. | |
| 6,839,586 B2 | 1/2005 | Webb | |
| 6,889,075 B2 | 5/2005 | Marchitto et al. | |
| 6,967,725 B2 | 11/2005 | Denk et al. | |
| 7,091,500 B2 | 8/2006 | Schnitzer | |
| 7,336,988 B2 | 2/2008 | Schnitzer | |
| 7,414,729 B2 | 8/2008 | Xie et al. | |
| 7,485,100 B2 * | 2/2009 | Garcia-Webb et al. | 600/587 |
| 8,068,899 B2 | 11/2011 | Llewellyn et al. | |
| 2002/0139920 A1 | 10/2002 | Seibel et al. | |
| 2002/0140942 A1 | 10/2002 | Fee et al. | |
| 2002/0141714 A1 | 10/2002 | Reed et al. | |
| 2002/0146202 A1 | 10/2002 | Reed et al. | |
| 2003/0031410 A1 | 2/2003 | Schnitzer | |
| 2003/0103262 A1 | 6/2003 | Descour et al. | |
| 2003/0117715 A1 | 6/2003 | Schnitzer | |
| 2003/0118305 A1 | 6/2003 | Reed et al. | |
| 2004/0143190 A1 | 7/2004 | Schnitzer | |
| 2004/0254474 A1 | 12/2004 | Seibel et al. | |
| 2004/0260148 A1 | 12/2004 | Schnitzer | |
| 2005/0157981 A1 | 7/2005 | Berier et al. | |
| 2005/0207668 A1 | 9/2005 | Perchant et al. | |
| 2005/0242298 A1 | 11/2005 | Genet et al. | |
| 2008/0297922 A1 | 12/2008 | Lule | |
| 2009/0012406 A1 | 1/2009 | Llewellyn et al. | |
| 2009/0323059 A1 | 12/2009 | Sun et al. | |
| 2010/0177389 A1 | 7/2010 | Rouyer | |
| 2011/0229840 A1 | 9/2011 | Liang et al. | |

OTHER PUBLICATIONS

Julian, F. J. and Morgan, D. L., "Intersarcomere dynamics during fixed-end tetanic contractions of frog muscle fibres," J Physiol 293, pp. 365-378 (1979).

Julian, F. J. and Moss, R. L., "Sarcomere length-tension relations of frog skinned muscle fibres at lengths above the optimum," J Physiol 304, pp. 529-539 (1980).

Freund et al. "Connective Tissue Polarity: Optical Second-harmonic Microscopy, Crossed-beam Summation, and Small-angle Scattering in Rat-tail Tendon," Biophysical Journal 50, pp. 693-712 (Oct. 1986).

Delp, S.L. et al., "An Interactive Graphics-based Model of the Lower Extremity to Study Orthopedic Surgical Procedures." IEEE Trans Biomed Eng 37, pp. 757-767 (1990)).

"Imaging and Optical technology at Aberdeen," Optics and Laser Technology 25(6), pp. 399-405 (1993).

Edman, K. A., Caputo, C. and Lou, F., "Depression of tetanic force induced by loaded shortening of frog muscle fibres." J Physiol 466, pp. 535-552 (1993).

Lieber et al. "In Vivo Measurement of Human Wrist Extensor Muscle Sarcomere Length Changes." Journal of Neurophysiology 71(3), pp. 874-881 (Mar. 1994).

Friden, J. and Lieber, R. L., "Physiologic consequences of surgical lengthening of extensor carpi radialis brevis muscle-tendon junction for tennis elbow," J Hand Surg [Am] 19, pp. 269-274 (1994), Abstract Only.

Shaw et al., "Infrared spectroscopy of dystrophic mdx mouse muscle tissue distinguishes among treatment groups," J. Applied Physiol. 81, pp. 2328-2335 (1996).

Guo et al. "Second-harmonic Tomography of Tissues," Optics Letters 22(17), pp. 1323-1325 (Sep. 1, 1997).

Lieber, R. L., Ljung, B. O. and Friden, J., "Sarcomere length in wrist extensor muscles. Changes may provide insights into the etiology of chronic lateral epicondylitis," Acta Orthop Scand 68, pp. 249-254 (1997).

Dutton, Harry, J.R., "Understanding Optical Communications," IBM, International Technical Support Organization http://www.redbooks.ibm.com, Sep. 1998.

Ljung, B. O., Friden, J. and Lieber, R. L., "Sarcomere length varies with wrist ulnar deviation but not forearm pronation in the extensor carpi radialis brevis muscle," J Biomech 32, pp. 199-202 (1999).

Guo et al., "Subsurface tumor progression investigated by noninvasive optical second harmonic tomography," Proc. Nat'l. Academy of Science 96, pp. 10854-10856 (Sep. 1999).

Moreaux et al., "Coherent Scattering in Multi-Harmonic Light Microscopy," Biophysical Journal 80, pp. 1568-1574 (Mar. 2001).

Mertz et al., "Second-harmonic generation by focused excitation of inhomogeneously distributed scatterers," Optics Communications 196, pp. 325-330 (2001).

Zoumi et al., "Imaging cells and Extracellular Matrix in vivo by using Second-harmonic Generation and two-photon excited fluorescence," PNAS 99(17), pp. 11014-11019 (Aug. 20, 2002).

Campagnola et al., "Three-Dimensional High-Resolution Second-Harmonic Generation Imaging of Endogenous Structural Proteins in Biological Tissues," Biophysical Journal 81, pp. 493-508 (Jan. 2002).

Gonzalez RV et al., "A real-time EMG-driven virtual arm," Comput. Biol. Med. 32(1) pp. 25-26 (Jan. 2002), Abstract Only.

Mohler et al., "Second-harmonic generation imaging of endogenous structural proteins," Methods 29, pp. 97-109 (2003).

Armstrong et al., "In vivo size and shape measurement of the human upper airway using endoscopic longrange optical coherence tomography," Opt. Express 11, pp. 1817-1826 (2003).

Brown et al. "Dynamic imaging of collagen and its modulation in tumors in vivo using second-harmonic generation." Nature Medicine 9, 796-800 (2003).

Jung et al., "Multiphoton endoscopy," Optics Letters 28(11), pp. 902-904 (Jun. 2003).

Konig et al., "High-resolution multiphoton tomography of human skin with subcellular spatial resolution and picosecond time resolution," Society of Photo-Optical Instrum. Engineers (2003), Abstract Only.

Levene et al., "In vivo multiphoton microscopy of deep brain tissue," J. Neurophysiol. 91, pp. 1908-1912 (Dec. 2003).

Zipfel et al., "Live tissue intrinsic emission microscopy using multiphoton-excited native fluorescence and second harmonic generation," PNAS 100(12), pp. 7075-7080 (Jun. 2003).

Campagnola et al., "Nonlinear Optical Spectroscopy," Optics & Photonics News, pp. 40-45 (Jun. 2003).

Anderson, et al., "Contributions of muscle forces and tow-off kinematics to peak knee flexion during the swing phase of normal gait: an induced position analysis," Journal of Biomechanics 37, pp. 731-737 (2004).

Jung et al., "In vivo mammalian brain imaging using one- and two-photon fluorescence microendoscopy," J. Neurophysiol. 92, pp. 3121-3133 (May 2004).

Mertz, J., "Nonlinear microscopy: New techniques and applications," Current Opinion in Neurobiology 14, pp. 610-616 (2004).

Niell et al., "Live Optical Imaging of Nervous System Development," Annu. Rev. Physiol. 66, pp. 771-798 and C1-C5 (2004).

Boulesteix et al., "Second-harmonic Microscopy of Unstained Living Cardiac Myocytes: Measurements of sarcomere length with 20-nm accuracy," Optics Letters 29(17), pp. 2031-2033 (Sep. 1, 2004).

(56) References Cited

OTHER PUBLICATIONS

Chu et al., "Studies of $X^{(2)}/X^{(3)}$ Tensors in Submicron-Scaled Bio-Tissues by Polarization Harmonics Optical Microscopy," Biophysical Journal 86, pp. 3914-3922 (Jun. 2004).
Williams et al., "Interpreting Second-Harmonic Generation Images of Collagen I Fibrils," Biophysical Journal 88, pp. 1377-1386 (Feb. 2005).
Flusberg et al., "In Vivo Brain Imaging Using a Portable 3.9 Gram Two-photon Fluorescence Microendoscope," Optics Letters 30(17), pp. 2272-2274 (Sep. 2005).
Helmchen et al., "Deep Tissue two-photon microscopy," Nature Methods 2(12), pp. 932-940 (Dec. 2005).
Lieber et al., "Biomechanical properties of the brachioradialis muscle: Implications for surgical tendon transfer," The Journal of Hand Surgery 30A(2), pp. 273-282 (Mar. 2005).
Rothstein et al., "Skeletal Muscle NAD(P)H Two-photon fluorescence microscopy in vivo: Topology and Optical inner filters," Biophysical Journal 88, pp. 2165-2176 (Mar. 2005).
Fu et al., "Integration of a Double-clad Photonic Crystal Fiber, a GRIN lens and a MEMS mirror for nonlinear optical endoscopy," BIO Meeting, Fort Lauderdale (Mar. 19, 2006).
Fu et al., "Nonlinear optical endoscopy based on a double clad photonic crystal fiber and a MEMS mirror," Optics Express 14, No. 3, pp. 1027-1032 (Feb. 2006).
Lee et al., "Integrated semiconductor optical sensor for chronic, minimally-invasive imaging of brain functions," Proceedings of the 28th IEEE, pp. 1025-1028 (Aug.-Sep. 2006).
Monfared et al., "In Vivo Imaging of Mammalian Cochlear Blood Flow Using Fluorescence Microendoscope," Otology and Neurotology 27, pp. 144-152 (2006).
Nucciotti et al., "Functional imaging of muscle cells by Second Harmonic Generation," Proc. of SPIE 6089, pp. 608911-1-608911-8 (2006).
Panchangam et al., "A novel optical imaging system for investigating sarcomere dynamics in single skeletal muscle fibers," Proc. of SPIE 6088, pp. 608808-1-608808-11 (2006).
Plotnikov et al., "Characterization of the Myosin-based source for Second-Harmonic Generation from muscle sarcomeres," Biophysical Journal 90, pp. 693-703 (Jan. 2006).
Rothstein et al., "Multi-photon excitation microscopy in intact animals," Journal of Microscopy 22(Pt. 1), pp. 58-64 (2006).
Plotnikov et al., "Optical Clearing for Improved Contrast in Second Harmonic Generation Imaging of Skeletal Muscle," Biophysical Journal 90, pp. 328-339 (Jan. 2006).
Murray, W. M., Hentz, V. R., Friden, J. and Lieber, R. L., "Variability in surgical technique for brachioradialis tendon transfer. Evidence and implications," J Bone Joint Surg Am 88, pp. 2009-2016 (2006).
Messerschmidt et al., "Novel concept of GRIN optical systems for high resolution microendoscopy. Part 1: Physical aspects," Proc. of SPIE 6432, pp. 643202-1-643202-9 (2007).
Ponten et al., "Intraoperative muscle measurements reveal a relationship between contracture formation and muscle remodeling," Muscle & Nerve 36, pp. 47-54 (Jul. 2007).
Schenkl et al., "Applications of rigid and flexible GRIN-endoscopes," Proc. of SPIE 6433, pp. 64330N-1-64330N-7 (2007).
Delp et al., "OpenSim: Open-Source Software to create and analyze dynamic simulations of movement," Biomedical Engineering IEEE 54, pp. 1940-1950 (Nov. 2007), Abstract Only.
Plotnikov et al., "Measurement of muscle disease by quantitative second-harmonic generation imaging," J. Biomed. Opt. 13 (Aug. 2008), Abstract Only.
Llewellyn, M. E., Barretto, R. P., Delp, S. L. and Schnitzer, M. J., "Minimally invasive high-speed imaging of sarcomere contractile dynamics in mice and humans," Nature 454, 784-788 (2008).
Gollapudi, S. K. and Lin, D. C., "Experimental determination of sarcomere force-length relationship in type-I human skeletal muscle fibers," J Biomech 42, pp. 2011-2016 (2009), Abstract Only.
Infantolino, B. W., Ellis, M. J. and Challis, J. H., "Individual sarcomere lengths in whole muscle fibers and optimal fiber length computation," Anat Rec (Hoboken) 293, pp. 1913-1919 (2010).
Smith, L. R., Lee, K. S., Ward, S. R., Chambers, H. G. and Lieber, R. L., "Hamstring contractures in children with spastic cerebral palsy result from a stiffer extracellular matrix and increased in vivo sarcomere length," J Physiol 589, pp. 2625-2639 (2011).

* cited by examiner

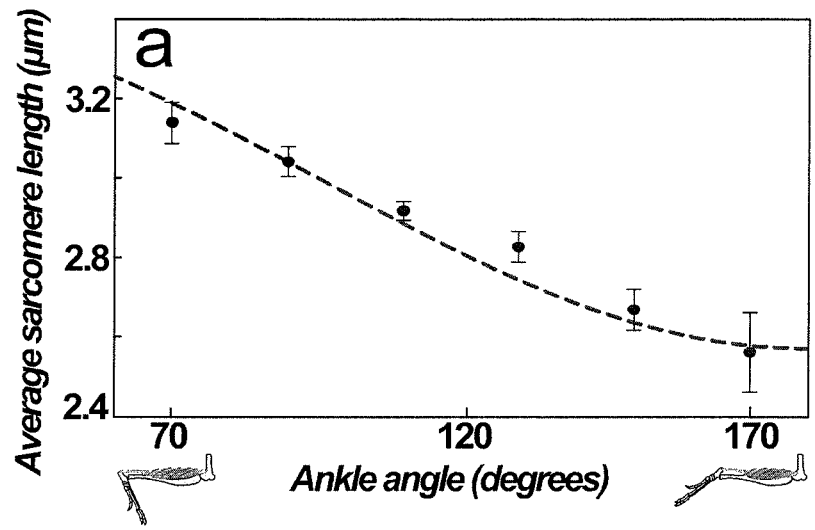
FIG. 6A
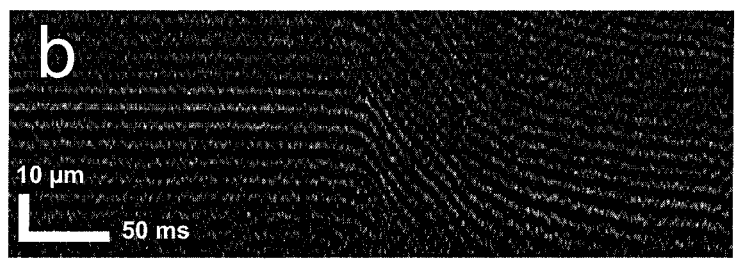
FIG. 6B
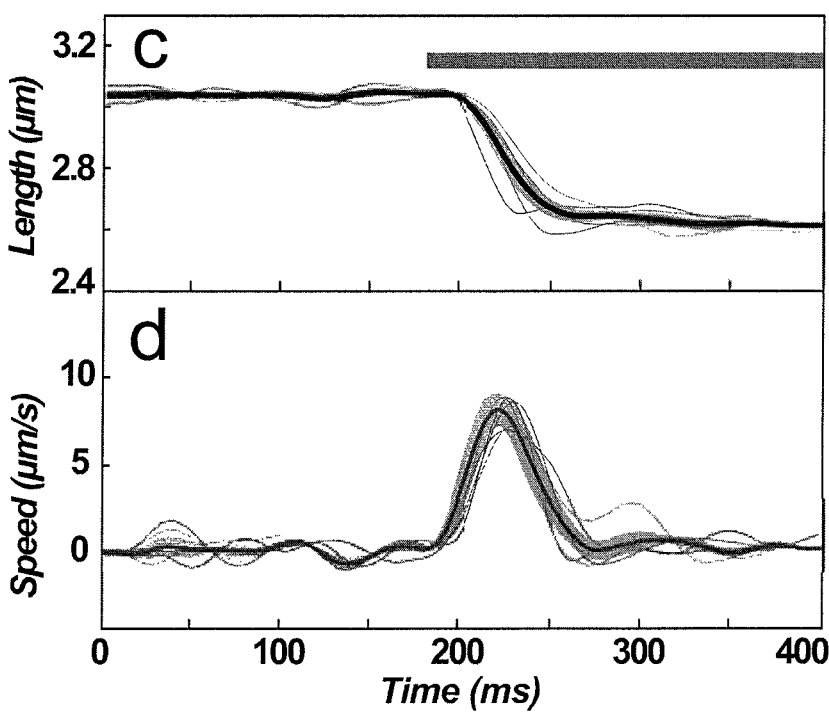
FIG. 6C
FIG. 6D

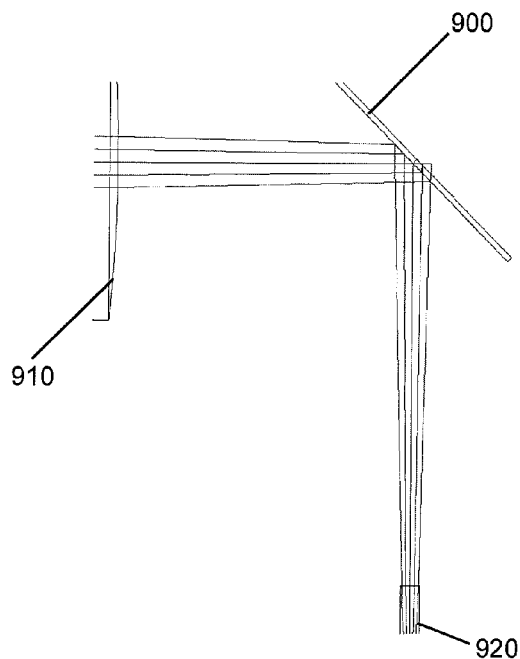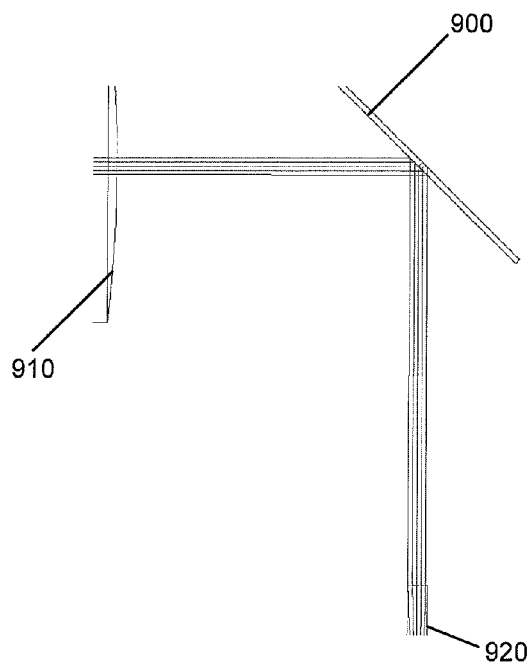
FIG. 9A  FIG. 9B
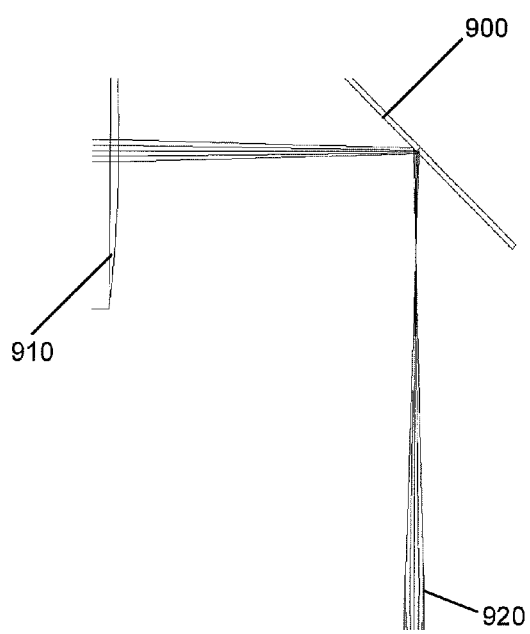
FIG. 9C

SYSTEM AND METHOD USEFUL FOR SARCOMERE IMAGING VIA OBJECTIVE-BASED MICROSCOPY

This patent document is a continuation-in-part under 35 U.S.C. §120 of U.S. patent application Ser. No. 12/165,977 filed on Jul. 1, 2008 (U.S. Pat. No. 8,068,899), which claims the benefit under 35 U.S.C. §119(e) of U.S. Provisional Patent Application Ser. No. 60/947,769 filed on Jul. 3, 2007; these patent documents, including the Appendix filed in the underlying provisional patent application, are fully incorporated by reference.

FIELD OF THE INVENTION

The present invention relates generally to biomedical cellular-level imaging systems and methods and more specifically to minimally-invasive systems and methods for characterizing biological thick tissue as a function of properties that are intrinsic to the tissue.

BACKGROUND

Biomedical-engineering advancements have provided a variety of tools to explore the detailed structure and behavior of biological tissues. Traditional equipment in this area has provided images and other data by way of x-rays, sound waves, and visible and infrared (IR) light to characterize the structure and behavior of certain tissues. Although generally successful, the image quality provided by such conventional equipment is limited and not applicable to all types of biological tissues. As examples, x-ray equipment typically transmits relatively low-level radiation and is used to characterize the location of the tissue as a function of its periphery, and visible/IR light imaging tools are used for characterizing transparent and semi-transparent tissue but are ineffective for imaging optically-dense ("thick") tissue.

Conventional approaches for high-resolution images of thick tissue have not been widely implemented due to approach-specific issues. Generally, these approaches can be categorized as "transmission-mode" (a.k.a., "forward-direction") systems and "reverse-direction" systems. Transmission-mode systems radiate energy at the tissue from one side and use a nearby sensing device on the opposite side of the tissue to sense the radiated energy after it is impacted by the tissue. One form of forward-direction imaging relies on SHG (second harmonic generation) which is known to be a forward-directed nonlinear optical process. In SHG, a light source directs photons at a target material for interacting and combining into higher-energy photons. The higher-energy photons are predominantly forwardly-directed at a sensing device on the opposite side of the tissue. While useful for many in vitro applications, this transmission-mode approach can be extremely invasive due to the need for a sensing device on the opposite side of the tissue. In more tissue-sensitive applications such as in vivo examinations and in vitro investigations where the integrity of the tissue is to be maintained after examination, this approach would be unacceptable due to the placement of the sensing device deep within the subject under examination.

Reverse-direction systems radiate energy at the tissue from one side and use a sensing device on the same side of the tissue to sense energy radiated in response. Unlike transmission-mode systems, these systems do not require placement of a sensing device on the opposite side of the tissue and therefore could be considered less invasive for in vivo applications. For high-resolution imaging of thick tissue, however, these systems require relatively strong signals and can require pre-treatment of the tissue with a foreign matter (e.g., dye, exogenous gene or protein) in order to enhance signals responding to excitation of the tissue by light. Such pre-treatment is undesirable for reasons concerning the invasiveness of the foreign matter and its alteration of the cells under examination.

Recent attempts to use reverse-direction systems have not been widely adopted. These attempts have relied on back-directed SHG or on endogenous (or native) fluorescence for tissue characterization for a variety of reasons. These approaches are burdened by insufficient signal strengths and/or the need to physically mitigate physiological motions associated with blood flow and respiratory activity. For imaging skeletal and/or cardiac muscle tissues, motions associated with sarcomere contractions further perturb image quality.

SUMMARY

The present invention is directed to methods for using and arrangements involving an optical probe for characterizing biological thick tissue. Certain applications of the present invention are directed to overcoming the above-mentioned limitations and addressing other issues as may become apparent in view of the description herein.

The present invention provides significant bio-medical high-resolution imaging advancements with minimally-invasive optical-probe implementations that produce high-resolution images of biological thick tissues using predominantly intrinsic biocellular sources. One example embodiment of the present invention uses a microendoscopic probe inserted, like a needle, as part of a minimally-invasive imaging procedure for stimulating structures intrinsic to the thick tissue. The probe is also used to collect the resulting signal for characterization of the tissue structure. The optical probe scans the thick tissue at a line resolution rate that is sufficiently-fast to mitigate motion artifacts due to contractile motion and/or physiological motion. In this context, a high-resolution imaging application produces images at sarcomere-level with subcellular detail and subcellular detail of other structures, while mitigating motion artifacts due to contractile motion and/or physiological motion such as respiration and blood flow. Certain example embodiments are implemented in vivo.

According to a particular embodiment of the present invention, the bio-medical imaging involves a reverse-direction operation. Such implementations, in accordance with the present invention, produce high-resolution images of biological thick tissues using a minimally-invasive optical probe to sense relevant intrinsic signals, thereby avoiding problems associated with pre-treatment of the tissue with a foreign matter, such as fluorescent dye, exogenous gene or protein.

According to more specific embodiments, the characterization can be in any of various forms which are sometimes application-dependent and/or dependent on the tissue. For instance, in one specific application, an optical probe is inserted into skeletal muscle. Light pulses transmitted by the probe stimulate the generation of signals, such as fluorescence and/or SHG, from intrinsic properties of certain tissue structures. These signals are collected and then processed to provide information such as sarcomere lengths, mobility, and indications of tissue dysfunctionality. This information can be provided in forms including displayed forms, for example, reports, units of measure and biological reproduction images, as well as non-displayed forms such as stored electronic data useful for latent processing.

According to certain example embodiments of the present invention, a system is implemented for visualizing sarcomeres in vivo. The system includes an optical probe having a light-pulse generator to send light pulses from the optical probe to certain targeted structure in the tissue. A photosensor senses, in response to the light pulses, selected signals generated from the sarcomere tissue and predominantly present due to properties intrinsic to the targeted structure. A signal processor is communicatively coupled to the optical probe to characterize the sarcomere tissue based on the sensed selected intrinsic signals.

In more specific embodiments, the light pulses from the light-pulse generator are tuned to a wavelength that interacts with the properties intrinsic to the tissue structure. The selected signals are generated from fluorescent mitochondrial molecules or from SHG.

The above summary is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which:

FIGS. 6A-6D are representations of images showing the dynamics of sarcomere contradictions, also consistent with the present invention;

FIGS. 9A-C show a constant beam waist at the back aperture of a GRIN endoscope, consistent with the present disclosure;

Figure 1A:
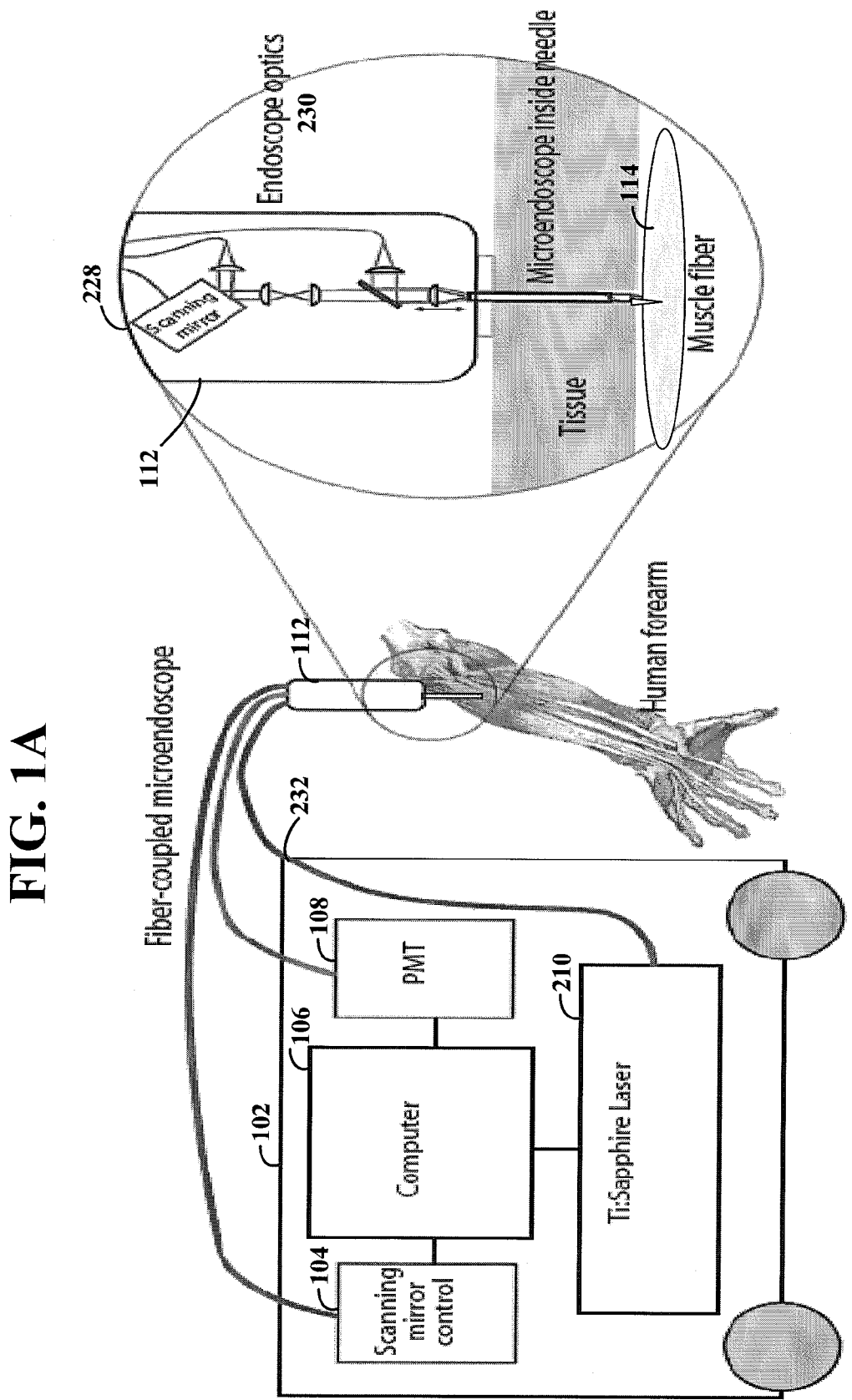
FIG. 1A illustrates an endoscopic imaging system adapted to excite structure(s) with optical signals (e.g., fluorescent NADH (nicotinamide adenine dinucleotide) or SHG signal) within certain thick tissue structures and to collect resulting intrinsic signals in response, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for a variety of different thick-tissue evaluation applications, and the invention has been found to be particularly suited for use in minimally-invasive medical applications, arrangements and methods which are benefited from high-resolution details of the thick tissue under examination. As discussed in the background above, these biomedical approaches include, but are also not necessarily limited to, in vivo examinations. Various aspects of the invention may be appreciated through a discussion of examples using this context.

In connection with various aspects of the present invention, it has been discovered that motion artifacts can be avoided by increasing the line scan rate as a function of the sarcomere dynamics and physiological motion, and the ability to collect the responsive signals that are predominantly present due to properties intrinsic to the structure. As these signals are typically weak and extremely difficult to detect, even by the most sophisticated of microendoscopes, controlling the line scan rate can be important for high resolution images of biological structure in and around sarcomere. Consistent with an important aspect of various embodiments of the present invention, unexpected high resolution images of this sarcomere-related structure are obtained by setting the scan rate to substantially minimize motion artifacts while permitting for the collection of these weak intrinsic-based signals.

In a more specific embodiment, images of sarcomeres and sub-cellular structures are obtained by using the optical probe to send light pulses toward structure in the biological thick tissue at a sufficiently fast line-resolution rate to mitigate motion artifacts due to sarcomere dynamics and physiological motion. This rate being sufficiently fast to cause (in response to the light pulses) signals to be generated from and across a sufficient portion of the structure to span a sarcomere length, and to collect selected aspects of the generated signals that are predominantly present due to properties intrinsic to the structure.

Consistent with one example embodiment of the present invention, an apparatus permits for very-high resolution characterization of cellular-level structure in thick tissue in a manner that is minimally invasive. The apparatus is capable of reverse direction imaging without staining or otherwise introducing a foreign element used to generate or otherwise increase the sensed light. The apparatus has a probe that includes a light generator for generating light pulses that are directed towards certain structures located within the thick tissue. The light pulses interact with intrinsic characteristics of the tissue structures to generate a signal. An emitted-light collector collects light (e.g., excited light or light based on SHG) used to characterize aspects of the thick tissue. Reliance on intrinsic characteristics of the tissue structures is particularly useful for applications in which the introduction of foreign substances to the thick tissue is undesirable, such as in human imaging.

Consistent with another embodiment of the present invention, the light generator and sensor are used in vivo using a probe, such as a needle or similar injection device, to minimize invasiveness while collecting sufficient cellular-level information for detailed visualizations. In vivo applications can be subject to image artifacts resulting from movement of the target animal. The light is directed from the aperture of the probe to the targeted thick tissue. The probe includes a light collector with a light-directing lens arrangement designed to provide a probe diameter that is sufficiently-small (in a specific example embodiment, about 1 mm to about 0.35 mm) to permit for needle-like insertion of the probe into the targeted thick tissue. For non-SHG applications, the probe has an objective with a numerical aperture (NA) and other attributes adequate for collecting intrinsic-based signals.

In connection with the present invention, certain embodiments use a probe to capture relatively low-intensity, intrinsically-based signals for a bright image with fine details of tissue structure, such as sarcomeres, while being sufficiently-narrow to be implemented in needle-like dimensions for microendoscopic applications performed in vivo.

According to experimental example embodiments, the above-described scopes have been implemented using three example sizes of gradient refractive index (GRIN) lenses: 1000, 500 and 350 microns O.D. To fit inside a needle for endoscopic delivery, the following commercially-available needles can be used:

| endo | needle | needle ID | needle OD |
|------|--------|-----------|-----------|
| 1000 | 16-18 Ga | 1070-1270 micron | 1270-1650 microns |
| 500  | 21-23 Ga | 510-570 micron | 640-820 microns |
| 350  | 24-25 Ga | 370-410 micron | 510-570 microns |

Such needles are available, for example, from Popper & Sons, New Hyde Park, N.Y.

In some applications, two-photon fluorescence microendoscope probes are implemented with minimally invasive compound GRIN lenses with flexible fiber-optic technology.

In another instance, the present invention is implemented in a reverse-direction system using a light generator and sensor located in close proximity. Proximity can be measured as either a spatial distance or as an angle relative to the direction of the light generated by the light generator. In one particular instance, the sensed signal is the result of fluorescence generated from excitation of the cell structure (e.g., from the mitochondria). Because fluorescence is an isotropic phenomena, the light is equally dispersed. Accordingly, the angle of the sensor relative to the light pulses need not be a critical consideration.

In another instance, the sensed light is the result of the light pulses passing through the cell structure and creating an SHG signal. The SHG signal is dependent on the light pulses, and the direction of the light pulses is relevant to the direction of the SHG signal. It has been discovered that an SHG signal can sometimes be classified into three components including forward directed, backscattered and backward directed. A forward directed SHG signal includes the signal components that continue in the direction of the light pulses. A backscattered SHG signal includes the signal components resulting from scattering of a forward directed SHG signal such that the SHG signal travels towards the light generator and sensor. A backward directed SHG signal includes the signal components that are directed opposite the direction of the originating light pulses without scattering. Thus, the placement of the sensor affects the relative collection efficiencies of the SHG signal components that are received. For instance, the placement of the sensor in the path of the backward directed SHG signal component can be particularly useful in reverse-direction systems (e.g., by facilitating the sensing of both the backward directed SHG signal and the backscattering SHG signal).

Turning now to the figures, FIG. 1A illustrates an endoscopic imaging system adapted to excite optical signals based on intrinsic thick tissue structures and to collect intrinsic signals in response. The system facilitates high-resolution imaging of thick tissue in vivo. Femto-second laser pulses (e.g., 80-150 fs) are generated by a laser 210. In a particular instance, the laser is a Ti-sapphire laser generating light with a wavelength around 700 nm to 1000 nm. The particular wavelength can be selected depending upon the application.

Due to the frequency-doubling characteristic of intrinsic SHG signals, the frequency of the SHG signal is directly proportional to the frequency of the excitation light (generated pulses). Thus, the generated pulses can be selected to minimize tissue absorption and scattering of the SHG signal for in vivo applications. Microendoscopic probe 112 acts to both direct the generated pulses and collect the intrinsic signals. This means that for fluorescent and SHG signals, the imaging process relies primarily upon backward directed/scattered (low-energy) light.

For intrinsic fluorescent and SHG signals, the probe can be inserted in close proximity to the targeted tissue or, as shown by muscle fiber 114, inserted into the targeted tissue. For isotropic light, the amount of light collected by a given collector changes relative to the distance from the source. Moreover, absorption and scattering of light from surrounding tissue increases as the distance from the source increases (the scattering length is about five times shorter than the absorption length). For approaches directed to SHG signal generation, it has been discovered that the SHG signal collected by a probe aligned with the excitation light generator (e.g., collecting backward SHG signals) and in close proximity to the thick tissue is surprisingly strong. This is particularly useful for non-invasive and minimally-invasive in vivo imaging. The imaging time can also be increased to increase the total amount of light received; however, increased imaging time can lead to increased susceptibility to physiological motion resulting in unwanted motion artifacts in the image.

Physiological motion, such as respiration and blood flow, are compensated for using a number of techniques. Using one such technique, microendoscopic probe 112 is inserted into the thick tissue. The probe 112 is small enough to allow physiological motion of the thick tissue to cause corresponding motion in the probe 112, while still capturing the imaging signals as discussed above. Thus, the effects of such physiological motion are mitigated by corresponding motion in the probe 112. The amount of allowable physiological motion can be estimated from the desired image resolution. For example, subresolution physiological motion would minimally affect subsequent image quality. The relevant amount of physiological motion is dependent upon the resolution of the desired image. For instance, images having a resolution on the order of a few micrometers are not substantially affected by physiological motion where the imaging is directed over a smaller span, e.g., much less than about 1-2 micrometers. Other factors that would affect the correlation between physiological motion and probe motion include the depth of the thick tissue, the length of the probe, and the stiffness of the optical fibers and the physical properties of the thick tissue.

In one embodiment, microendoscopic probe 112 is connected to control arrangement 102 using fiber cables and control lines for scanning, whereas in other embodiments physical separation is not provided (e.g., by fiber cables). Control arrangement 102 includes various light generation and detecting components controlled by a processor/computer 106. In a particular instance, light generation block 210 (e.g., a Ti:Sapphire laser) produces light pulses that are transmitted to probe 112 using fiber optics, and photomultiplier tube (PMT) block 108 receives light collected by probe 112 using fiber optics. The use of a flexible light-transport medium is useful because probe 112 can be moved independently relative to the position of light generation block 210 and PMT block 108. Scanning mirrors 228 provide directional control over the light pulses. Endoscope optics 230 directs both the transmitted light pulses and the corresponding collected light.

As discussed above, to minimize the size of the probe, the probe should be sufficiently small and the objective and related optical properties of the probe should be able to capture the intrinsic-based signals. In a specific example, the probe is a gradient refractive index (GRIN)-lens microendoscopic probe used to provide a minimally-invasive mechanism for imaging such signals in thick tissue in vivo. In another more specific embodiment, rather than securing both the probe and the subject, the probe can be allowed to move with the thick tissue. This freedom of movement is particularly useful for reducing motion artifacts due to physiological motion.

For many applications, it should be appreciated that the first priority is to be able to collect the intrinsic signals, and the second priority is to make the probe small enough without compromising the first priority; however, there are applications, such as where the target tissue is pre-exposed, that may be performed that do not necessarily have the small size requirement.

In one instance, the probe scans the thick tissue using a scanning device to direct light pulses toward the thick tissue. One such scanning device is a micro-electro-mechanical systems (MEMS) mirror. Scanning mirror control 104 provides signals to control the scanning device. The size of the scanning device is also a component of the overall size of the probe.

In one specific example application involving visualization of dynamic sarcomeres, a system as illustrated in connection with FIG. 1A is used to obtain images based on line-scan speeds of about 2 kHz, with each line being 256 pixels long and a dwell time of 2 μsec. During imaging, each line is approximately 0.512 msec. To prevent damage to the tissue by the laser, the power is limited to less than 50 mW incident at the sample. In other embodiments, the SHG signal is boosted by increasing power, but too much power might damage the tissue. With a limit on the signal being generated at the sample and using desired (or optimized) optics for practically collecting the largest fraction of that signal, the signal-to-noise ratio (SNR) becomes a limiting factor. In one instance, the line scan is 2 KHz while still maintaining a reasonable SNR. These parameters are adequate for providing images of skeletal sarcomeres. In order to image faster, the noise is decreased or the fraction of the SHG signal (that is collected) is increased. When using a PMT, which has a relatively low noise, decreasing the noise further is not practical. To increase the fraction of the signal being collected, the NA of the GRIN lenses can be increased, e.g., from an NA of 0.46 to an NA of about 0.7; such an increase increases the fraction of SHG collected by a factor of about two. In another application, the dwell time is reduced to about 1 μsec and the scan rate is increased to about 4 kHz.

Other physiologic movements are caused by the heart beat and breathing which are about 1 Hz and 0.2 Hz respectively. By imaging at about 2 kHz, embodiments of the present invention allows for the collection of an entire image of 256 lines (0.13 sec) during a time when the animal is between heartbeats or breathing, thus practically eliminating motion artifacts. Assuming the same magnitude of signal is being generated from the skeletal muscle; applications of the present invention are useful for imaging a beating heart or organs in the thorax and abdomen.

Figure 2:
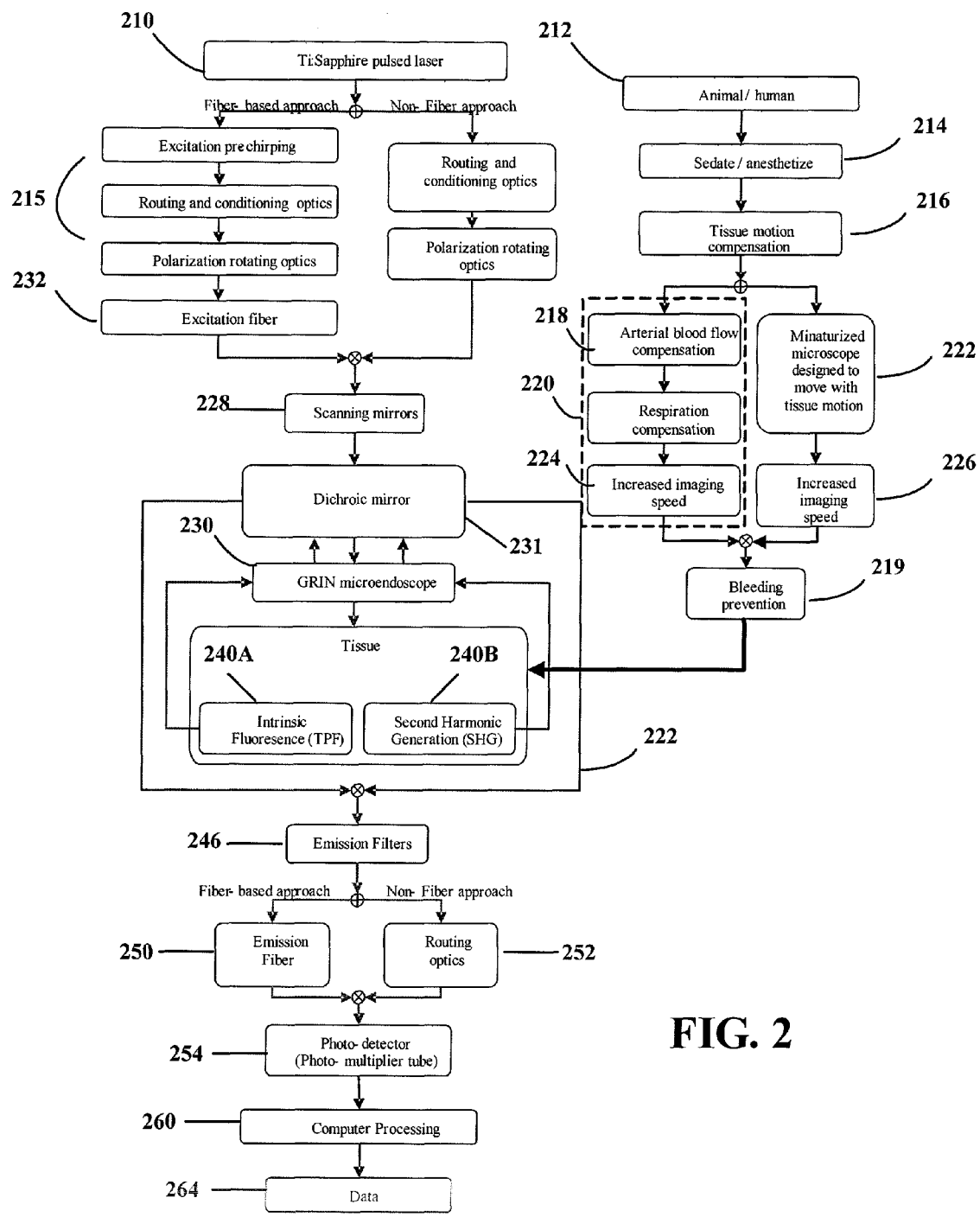
FIG. 2 shows a flow diagram depicting a method for use with an endoscopic imaging system adapted to excite optical signals based on intrinsic properties of thick tissue structures and to collect intrinsic signals in response, according to another example embodiment of the present invention.

FIG. 2 shows a flow diagram of a method for use with an endoscopic imaging system adapted to excite optical signals based on intrinsic thick tissue structures and to collect resulting intrinsic signals. The flow diagram shows two main paths, one beginning with the Ti:Sapphier pulsed laser 210 and the other beginning with the stabilized subject 212 (e.g., animal or human, typically in vivo). These paths show the operation of the imaging probe and the preparation of the subject, respectively.

Referring to the path beginning with block 212, stabilizing the subject to some degree can be important and useful for limiting movement that would interfere with medical oversight during the procedure as well as with the production of high-resolution images. In accordance with surgical procedures used as part of the present invention, such physical restraint optionally includes sedation (214) and/or conventional physical restraints (216) for limiting or controlling motion. At more detailed levels of tissue characterization, physical restraints can include conventional restraints to physiological motion such as by limiting blood flow (218-219) and respiration (220). In other embodiments (alone or in combination with those discussed herein), respiration compensation can be accomplished by sedation, holding one's breath or through forced ventilation timed so that pauses in the ventilation occur during the imaging process. Also consistent with various ones of the above embodiments, block 222 shows use of a microendoscope that is sufficiently small so that when it is inserted into the thick tissue, the microendoscope moves with the tissue thereby mitigating the effect of the motion.

As will be discussed below, certain embodiments of the present invention produce high-resolution images of significant thick tissue structure without requiring significant compensation for such motion. Consistent with the above-discussed aspects of the present invention and as depicted by blocks 224 and 226 of FIG. 2, such motion artifacts can be avoided by increasing the line scan rate as a function of the sarcomere dynamics and physiological motion, and the ability to collect the responsive signals that are predominantly present due to properties intrinsic to the structure. In this manner, sufficient intrinsic-based signals can be picked up by a commercial microendoscope for producing high-resolution images of structure in and around sarcomere, while mitigating artifacts caused by the sarcomere and related physiological motion.

In a more specific embodiment also according to the present invention, motion artifacts are mitigated as needed for the application at hand. In this manner, a computer-based digital imaging application uses conventional (e.g., standard-deviation) calibration techniques to discern the quality of the process. Should the data processing indicate that the sarcomere lengths cannot be discerned (i.e., insufficient resolution), the images are rejected as having unacceptable degrees of motion artifacts. The sarcomere length within an image is found by a computer algorithm, e.g., Fourier transform, wavelet transform or fitted sine-wave, such that a confidence interval is also generated for the measurements. In one application, an example threshold for an acceptable standard-deviation is about 5% (confidence interval is compared to an arbitrary value; +/−5% is commonly used, to discriminate between images that contain measurable sarcomere lengths from those that do not). Data-capture adjustments, whether automatically by the computer or manually by the system user, are then made and/or further imaging efforts are repeated.

Figure 1B:
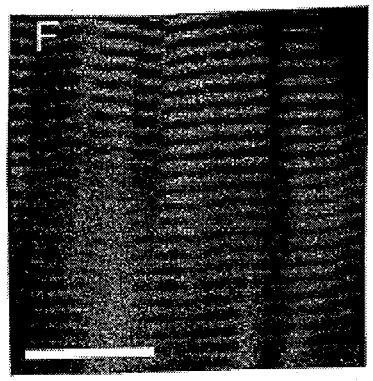
FIGS. 1B and 1C are images of animal tissue obtained in vivo via a microendoscopic probe according to an example embodiment of the present invention.
Figure 1C:
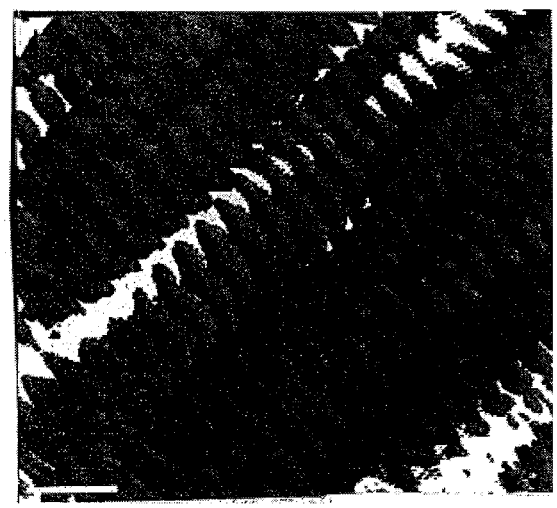

As examples of such detailed images obtained according to these embodiments of the present invention, FIGS. 1B and 1C are respective reproductions of images of sarcomere and subcellular structure. FIG. 1B is an image taken from in vivo mouse lateral gastrocnemius using a 350 μm endoscope. The scale bar indicates 25 μm. FIG. 1C is a three-dimensional reconstruction of lateral gastrocnemius muscle in a living mouse. The model was created from a stack of 1 μm thick images taken with a 350 μm endoscope in a living mouse using SHG. The scale bar indicates 10 μm.

With the microendoscope inserted in the subject 212, the laser 210 initiates the methodology by sending pulses through the microendoscope 230 while using a GRIN endoscope and excitation pre-chirping and optical signal processing as is conventional, as depicted at 215. Scanning mirrors 228 direct the pulses at the relevant tissue site, and dichroic mirrors are used to separate the excitation light from the emission light (block 231). The line-resolution rate is set sufficiently fast relative to the motion artifacts expected due to factors such as sarcomere movement and physiological motion. In a particular instance, the pulses are directed such that they capture the entire length of the sarcomere being imaged. Through the various techniques discussed herein, signals are generated in response to the pulsed light. These signals are collected by the probe and used as part of the data for creating the desired image. This process may be repeated as desired. For example, the multiple line scans may be used to generate larger imaging sections or to capture sequential images of the same sarcomere under different conditions. In a particular instance, the effectiveness of a form of therapy may be evaluated using images captured both before and after therapy is provided for the patient.

The path beginning with the pulsed laser 210 shows two approaches. A first approach (left path) involves fiber optics attached to a microendoscopic probe and a second approach (right path) is implemented without fiber optics. The fiber approach involves a first step of excitation pre-chirping to compensate for transmission over optical fiber (e.g., to reduce group-velocity-dispersion). The signal is then converted to the desired shape and path using conditioning optics and routed to polarization rotating optics. Upon polarization, the resulting femtosecond laser pulses are passed through an optical excitation fiber 232, such as a photonic crystal fiber. The second, non-fiber optics, approach operates much the same as the first approach without the need to compensate for transmitting the pulses through an optical fiber.

Once the optical pulses reach the microendoscopic probe, a scanning device (e.g., MEMS mirror) directs the pulses. A dichroic mirror allows light of a certain wavelength to pass, while reflecting light of another. Thus, the dichroic mirror separates the laser pulses (excitation light) from the intrinsic signals (emission light). The laser pulses are directed through the GRIN microendoscope and to the thick tissue. The laser/excitation pulses striking the thick tissue result in intrinsic signals (240A for intrinsic fluorescence (TPF) or 240B for SHG). The GRIN microendoscope 230 collects the intrinsic signals passing them to the dichroic mirror. The dichroic mirror routes the collected signals towards emission filters 246. The collected signals pass through emission fiber 250 and routing optics 252 (or fiber optics) to a photo-detector 254. The photo-detector 254 receives and detects the collected signal. A processor 260 running customizable software processes the information for producing the data 264 in response to the photo-detector and thereby permitting for structure visualization. In one instance, the software compensates for motion artifacts and an image of the thick tissue is then generated for viewing.

In one particular embodiment, a microscope objective focuses ultrashort pulsed laser illumination onto the face of a gradient refractive index (GRIN) microendoscope. The microendoscope demagnifies and refocuses the laser beam within the muscle and returns emitted light signals, which reflect off a dichroic mirror before detection by a photomultiplier tube (PMT). A 350-μm-diameter GRIN microendoscope clad in stainless steel can be used for minimally invasive imaging in the arm of a human subject.

For static imaging of individual sarcomeres, another embodiment provides images of a single mouse muscle fiber in culture, acquired using epi-detection of two-photon excited autofluorescence and band-pass filtered to highlight sarcomeres. As a variation, a band-pass filtered image of the same fiber can be obtained using trans-detection of second-harmonic generation (SHG). As an enhancement, overlaying the above two image types reveals that autofluorescence signals, thought to arise from mitochondria located mainly at the Z-discs of sarcomeres, interdigitate with the SHG signal thought to arise in myosin tails.

Optical probe systems described herein can be implemented as a microendoscope probing approach, according to the present invention, by using very small lens systems having an acceptable objective lens and overall diameters as described above. For instance, such microscopic endoscopes can be implemented using lens technology described in U.S. Pat. No. 5,161,063 and as described in other references including, but not limited to, technology that is commercially-available from a variety of manufacturers. One such manufacturer is Olympus (as cited in U.S. Pat. No. 5,161,063) which markets such scopes having diameters at about 700 microns; other acceptable microscopic endoscopes can be similarly constructed using miniature-sized lens. For further information regarding such systems, reference may be made to, "In Vivo *Imaging of Mammalian Cochlear Blood Flow Using Fluorescence Microendoscope*", Otology and Neurotology, 27:144-152, 2006, "In Vivo *Brain Imaging Using a Portable 3.9 Gram Two photon Fluorescence Microendoscope*", Optics Letters, Vol. 30, No. 17, Sep. 1, 2005, and the following U.S. Patent Publications: No. 2004/0260148 entitled "Multi photon endoscopic imaging system"; No. 2004/0143190 entitled "Mapping neural and muscular electrical activity"; No. 2003/0118305 entitled "Grin fiber lenses"; No. 2003/0117715 entitled "Graded-index lens microscopes"; No. 2003/0031410 entitled "Multiphoton endoscopy"; No. 20020146202 entitled "GRIN fiber lenses"; and No. 2002/0141714 entitled "Grin-fiber lens based optical endoscopes".

In certain systems and applications of the present invention, embodiments described herein include optical fiber arrangements, and in some applications, a bundle of optical fibers. Various example embodiments are directed to the use of optical fibers such as those described in the following U.S. Patent Publications: No. 2005/0157981 entitled "Miniaturized focusing optical head in particular for endoscope" (to Berier et al.), No. 2005/0207668 entitled "Method for processing an image acquired through a guide consisting of a plurality of optical fibers" (to Perchant et al.), No. 2005/0242298 entitled "Method and equipment for fiber optic high-resolution, in particular confocal, fluorescence imaging" (to Genet et al.) and No. 2003/0103262 entitled "Multimodal miniature microscope" (to Richards-Kortum et al.); and as those described in the following U.S. Pat. No. 6,766,184 (Utzinger et al.) entitled "Methods and apparatus for diagnostic multispectral digital imaging," U.S. Pat. No. 6,639,674 (Sokolov et al.) entitled "Methods and apparatus for polarized reflectance spectroscopy," U.S. Pat. No. 6,571,118 (Utzinger et al.) entitled "Combined fluorescence and reflectance spectroscopy," and U.S. Pat. No. 5,929,985 (Sandison et al.) entitled "Multispectral imaging probe". Each of these above-cited documents is fully incorporated herein by reference.

Various embodiments of the present invention are specifically directed to measurement of sarcomere lengths in healthy subjects and in individuals with neuromuscular diseases, allowing discovery of the mechanisms leading to disabling muscle weakness. For example, in the clinic, the device is used as a diagnostic tool to determine the cause of weakness.

The capacity of muscles to generate forces is highly sensitive to sarcomere length. Muscles generate their maximum force at a sarcomere length of approximately 3 µm, but generate almost no force at lengths of 2 µm or 4 µm. In some instances, profound weakness in patients with neuromuscular diseases, such as cerebral palsy, may be caused by altered sarcomere lengths. The ability to confirm this, in a variety of patient populations, enables important studies that examine the mechanisms of muscle weakness in persons with neuromuscular diseases.

In another example, implementations of the present invention are applied during surgery wherein this technology is used to set sarcomeres to the right length. The microendoscope is inserted into muscle in order to visualize and measure the sarcomere lengths and the related muscle-attachment points to provide maximum muscle strength following musculoskeletal surgeries. This approach is used to improve the outcome of tendon lengthenings, tendon transfers, joint reconstructions and other musculoskeletal reconstructions.

Another application is directed to cardiac health. Cardiac health is dependent on contraction of cardiac muscle cells and imaging of sarcomeres in a manner consistent with the above enables distinction of healthy and diseased or damaged cardiac tissue. The response to drugs may increase or decrease contractility, and imaging sarcomere dynamics, as enabled here, allows these assessments in living subjects and in vitro. In accordance with the present invention, the following discussion is illustrative of cardiac uses and applications.

Figure 3:
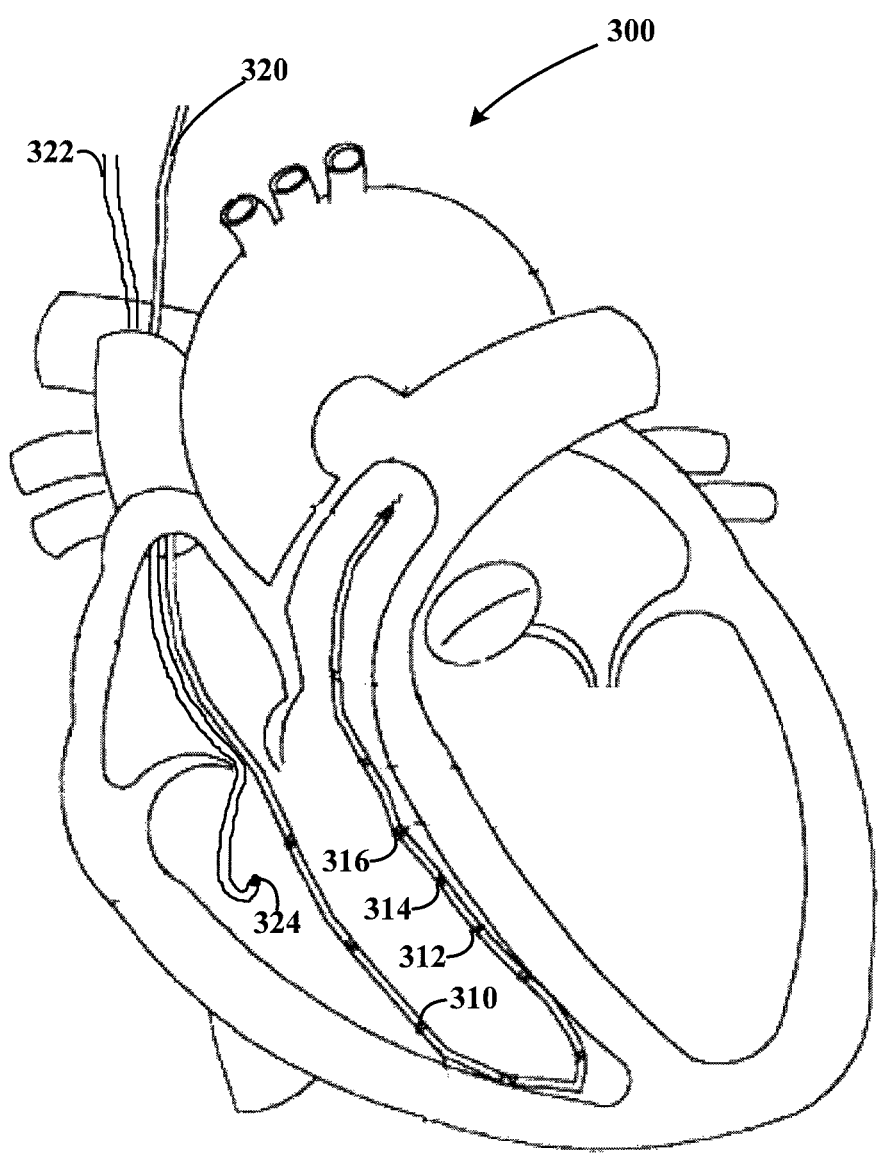
FIG. 3 shows an example implementation of the present invention for specific application for high-resolution imaging cardiac sarcomeres, with an optional stimulus step being provided for altering a condition of the heart and repeating certain steps to provide additional imaging assessing the biological tissue.

FIG. 3 depicts a heart 300 having a channel (or lead) 320 introduced to the heart for the purpose of altering a condition of the heart, according to one embodiment of the invention. Lead 320 includes electrodes 310-316 for delivering electrical stimulus or for sensing electrical properties of the heart. Lead 320 may be introduced to the heart using a number of different techniques. In this instance, lead 320 is shown as being introduced through the coronary artery. In one instance, a pacemaker device, located external to the heart, controls the electrical stimulus provided by electrodes 310-316. Images may be taken of myocardial sarcomeres using the various methods, systems and devices described herein. These images may include myocardium sarcomere as accessed via the endocardium or epicardium. In these applications, the above-discussed microendoscopes can be used to obtain such images via myocardium tissue accessible from areas outside the heart or, as with lead 322 and optical probe 324, areas within the heart. In the latter application, the same access port (e.g., the coronary artery) or another access port may be used.

Using the above approach for cardiac stimulating/monitoring with related cardiac imaging, various specific applications are realized. In a particular instance, images taken of the myocardial sarcomere without stimulus from the electrodes 310-316 are compared to images taken of the myocardial sarcomere with stimulus from electrodes 310-316. This may be particularly useful in assessing the effectiveness of a particular cardiac treatment. In another instance, images of various cardiac treatments can be compared. For instance, the effects of dual (atrial and ventral) stimulus may be compared against ventral only stimulus. In another instance, the location, voltage and pulse duration of the electrical stimulus may be varied to allow for a comparison of the respective myocardial sarcomere images. In other instances, damaged cardiac tissue can be imaged to ascertain the extent of the damage or to assess the effectiveness of a treatment of the damaged tissue.

In one embodiment, an input component is used to trigger the imaging time. Such an input component may originate from a number of sources. For instance, QRS signals of the heart, such as those captured by an electrocardiograph, may be used to trigger the imaging and/or as part of the system (e.g., using an EKG system concurrent with the imaging approach illustrated in FIG. 1A). In another example, signals originating from the pacemaker device can be used to trigger the imaging and/or capture the myocardium (via a pacing signal) while imaging the sarcomere and monitoring the effectiveness of the treatment. Such image-timing techniques can be useful for capturing images of myocardial sarcomere that correspond to natural heart function, captured heart contractions (e.g., electrode induced), and the like.

In other embodiments, the heart may be altered using other techniques and combinations of techniques. For instance, electrical stimulus need not be administered using the electrode/lead configuration displayed in FIG. 3. Instead, any number of techniques may be employed. Other heart altering therapies, such as drug induced alterations, may also benefit from the imaging of the myocardial sarcomere. For background discussion, reference can be made to any number of U.S. patents directed to cardiac monitoring and cardiac therapy.

In another cardiac-imaging application, a specific embodiment of the present invention is directed to the system shown in FIG. 1A modified to include a lead within the microendoscope probe to provide myocardium stimulus that is used concurrent with the above-described dynamic sarcomere imaging. For example, such microendoscope lead(s) can be combined with or within a single lead channel in which multiple signals are transmitted via the same lead channel for stimulation and monitoring purposes such as by modifying embodiments illustrated in U.S. Pat. No. 6,208,886, entitled "Non-linear Optical Tomography of Turbid Media" (e.g., see FIG. 9 showing multiple (send/receive) fibers in same channel).

Accordingly, this specific embodiment includes the system of FIG. 1A modified such that a lead channel simultaneously delivers the electrical leads (commonly used for cardiac stimulus) along with multiple (send/receive) optical fibers. The microendoscope probes are then used as described in connection with the above embodiments to provide myocardium stimulus and/or capture concurrently with the dynamic sarcomere imaging. By varying the timing, phases and power parameters of the myocardium stimulus, suspect (diseased) cardiac sarcomere can be viewed at detailed levels not previously recognized and thereby permitting patient-customized cardiac monitoring, therapy and/or pace-signal control for overall cardiac management.

Figure 4A:
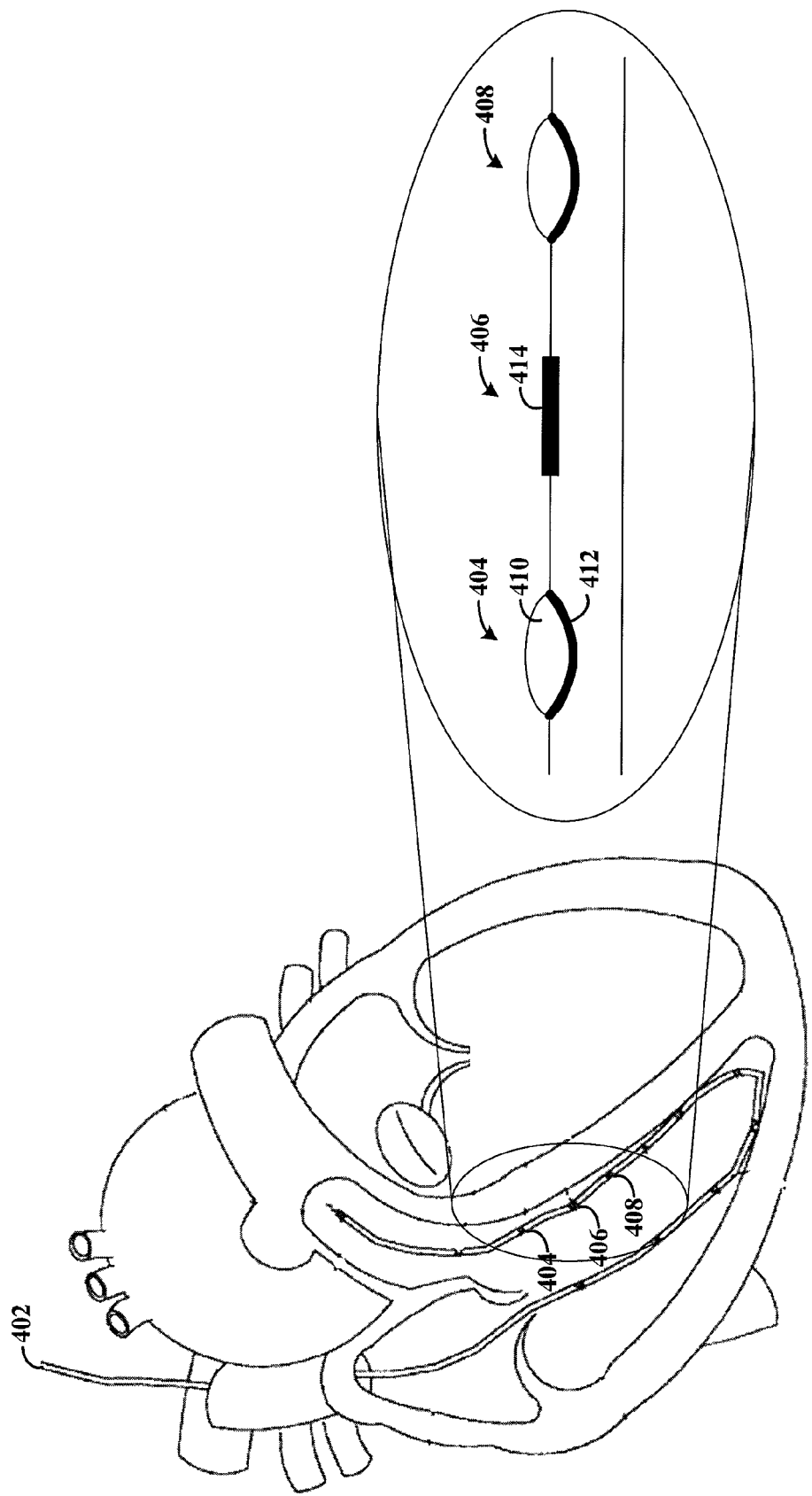
FIG. 4A-4D show lead channels that simultaneously deliver electrical leads (commonly used for cardiac stimulus) along with multiple (send/receive) optical fibers, according to various example implementations of the present invention.
Figure 4B:
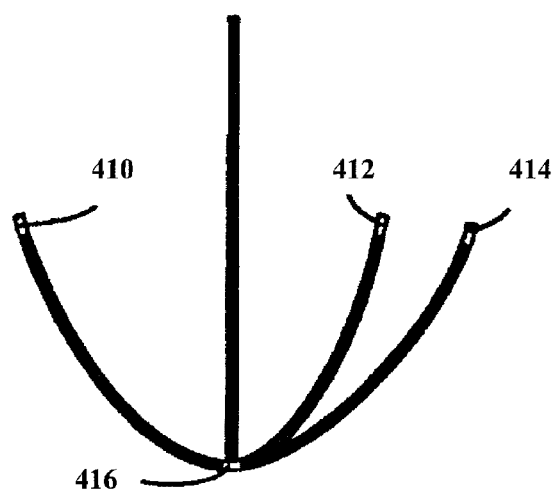
Figure 4C:
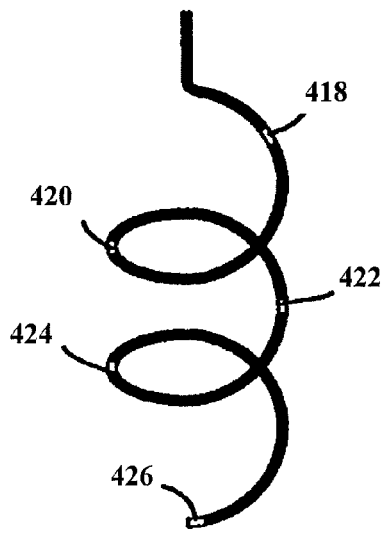
Figure 4D:
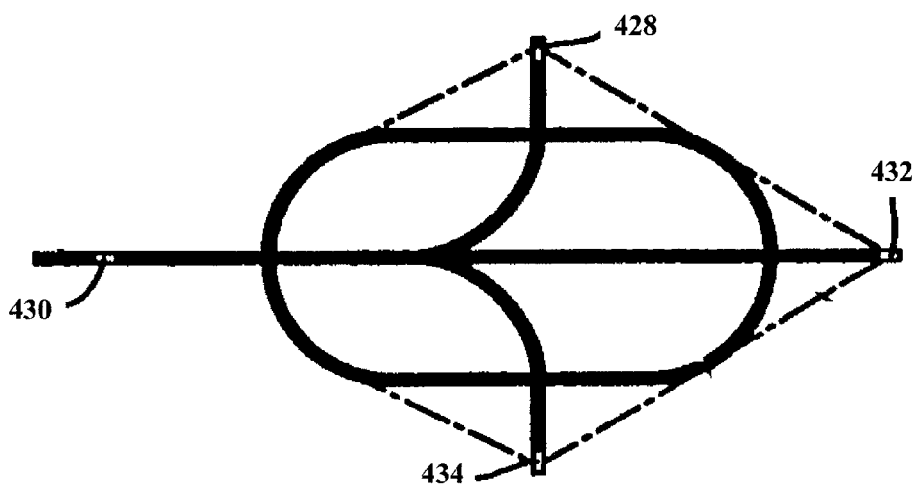

FIGS. 4A-4D illustrate such example approaches in accordance with the present invention. In each instance, a lead channel simultaneously delivers the electrical leads (commonly used for cardiac stimulus) along with multiple (send/receive) optical fibers. As shown in FIG. 4A, the channel 402 includes multiple nodes 404-408 at which electrodes 414 (such as 312 of FIG. 3) and/or microendoscopic probes (such as 112 of FIG. 1) access the myocardium. Where a node 404 includes both an electrode 410 and a microendoscopic probe 412 (i.e., the end of probe 112 of FIG. 1), the electrode can be implemented as a conductive terminal at or immediately adjacent to the probe. By using multiple ones of such nodes, control circuitry (for the electrodes and/or the optics) can be selectively enabled so as to explore and access different areas of the myocardium tissue without necessarily repositioning the channel 402. FIGS. 4B-4D illustrate various configurations for the channel 402 and the corresponding location of the nodes 410-434, which may be suitable for different applications. For further discussion relating to different configurations of the channel, reference may be made to U.S. Pat. No. 5,181,511 entitled "Apparatus and Method for Antitachycardia Pacing Using a Virtual Electrode" (e.g., see FIGS. 5 and 6A-6F), which is hereby fully incorporated by reference.

Additional Experimental Efforts and Related Embodiments.

Here, we report direct visualization of individual sarcomeres and their dynamical length variations using minimally invasive optical microendoscopy to observe second harmonic frequencies of light generated in the muscle fibers of live mice and humans. We imaged individual sarcomeres in both passive and activated muscle. Our measurements permit in vivo characterization of sarcomere length changes that occur with alterations in body posture and visualization of local variations in sarcomere length not apparent in aggregate length determinations. High-speed data acquisition enabled observation of sarcomere contractile dynamics with millisecond-scale resolution. These experiments evince in vivo imaging to demonstrate how sarcomere performance varies with physical conditioning and physiological state, as well as imaging diagnostics revealing how neuromuscular diseases affect contractile dynamics. Further, with such in vivo measurements of individual sarcomeres, we learn precisely the normal operating range or variability of sarcomere length, how physiological regulation may adjust sarcomere lengths, and/or how sarcomere lengths are disrupted in disease.

Figure 5:
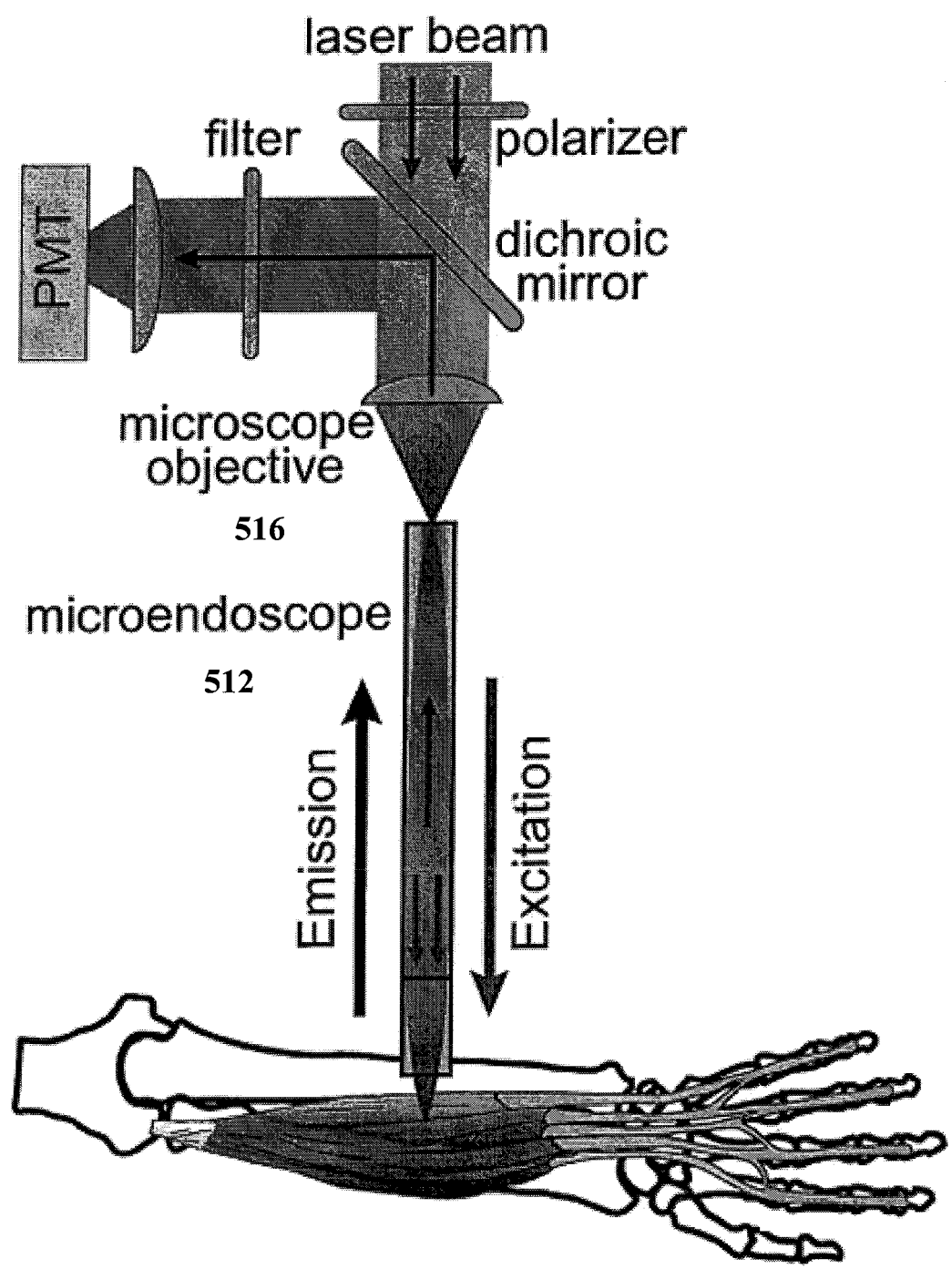
FIG. 5 is another endoscopic imaging system in accordance with the present invention.

In specific experimental embodiments, we use an optical microendoscope having gradient refractive index (GRIN) microlenses (350-1000 μm diameter), to enter tissue in a minimally invasive manner and provide micron-scale imaging resolution. To facilitate studies in humans, certain embodiments avoid use of exogenous labels and rather explore the potential for microendoscopy to detect two intrinsic optical signals. The first of these signals represents autofluorescence from nicotinamide adenine dinuclueotide (NADH) and flavoproteins, which are concentrated in mitochondria along sarcomere Z-discs. The other signal represents second-harmonic generation (SHG), coherent frequency-doubling of incident light, which occurs within myosin rod domains. Our instrumentation has used an upright laser-scanning microscope adapted to permit addition of a microendoscope 512 for deep tissue imaging (FIG. 5). A microscope objective 516 coupled the beam from an ultrashort-pulsed Ti:Sapphire laser into the microendoscope, to allow generation of two-photon excited autofluorescence and second-harmonic signals. In both cases signal photons generated in thick tissue returned back through the microendoscope 512 and were separated from the excitation beam based on wavelength (FIG. 2).

We started investigations by imaging autofluorescence and second-harmonic signals simultaneously from cultured muscle cells. The two signals were distinguishable by wavelength, the partial polarization of SHG signals and their dependence on incident light polarization, and the predominance of trans-(forward-propagating) over epi-detected (backward-propogating) SHG signals (Methods). With <30 mW of incident laser power, sarcomeres were readily apparent using either intrinsic signal, especially after band-pass filtering the images to remove spatial frequencies representing distance-scales outside the plausible range of sarcomere lengths (1-5 μm). Overlaid images of autofluorescence and second-harmonic signals revealed that the two arise spatially out of phase within sarcomeres, as expected if autofluorescence were to come mainly from Z-disc mitochondria and SHG from myosin rods.

For use in live subjects, we imaged based on epi-detected SHG and autofluorescence signals from the lateral gastrocnemius muscle of anesthetized adult mice. Although SHG primarily arises in the forward-propagating direction, we hypothesized that in thick tissue there would be sufficient backward-propagation to allow in vivo microendoscopy, due to multiple scattering of photons that were originally forward-propagating. We discovered that in vivo SHG imaging of sarcomeres was feasible by microendoscopy using illumination wavelengths of ~820-980 nm and generally led to better sarcomere visibility than autofluorescence imaging (see Methods, supra). SHG is an effective, endogenous contrast parameter that can be used to visualize sarcomeres in living subjects, and for subsequent imaging we used SHG and 920 nm illumination.

We further explored capabilities for imaging sarcomeres in anesthetized mice. After inserting a microendoscope into the gastrocnemius, we regularly imaged large assemblies of individual muscle sarcomeres (n=23 mice). Cardiac and respiratory movements often caused significant motion artifacts at image frame acquisition rates of <4 Hz, but at 4-15 Hz sarcomeres were readily identifiable within raw images. Insertion of the microendoscope helped stabilize underlying tissue, reducing tissue motion and enhancing image quality. To test the utility of our data, we performed several illustrative analyses of muscle fiber structure in live mammals.

First, we determined average sarcomere lengths and their variability within individual muscle fibers and between adjacent fibers. Uncertainties in measurements of average sarcomere length within individual fibers can be reduced to limits set by the inherent biological variability, rather than by instrumentation, since the distance spanned by a large, countable number of sarcomeres can be determined at a diffraction-limited resolution. Thus, with 20-50 nm sarcomeres often visible concurrently, our measurements of average sarcomere length have ~20-50 nm accuracy. In connection with the invention, we discovered that individual sarcomere lengths can be variable, with up to ~20% variations within a ~25-µm-diameter vicinity. The degree of local variability is likely influenced by passive mechanical inhomogeneities and could not be examined previously without a technique such as ours for visualizing individual sarcomeres.

We created three-dimensional models of muscle fiber structure from stacks of SHG images acquired at 0.5 µm depth increments within tissue. Construction of these models used the optical sectioning provided by SHG imaging which, like two-photon imaging, generates signals from a spatially restricted laser focal volume (see Campognola, P. J. et al., "*Three-dimensional High-resolution Second-harmonic Generation Imaging of Endogenous Structural Proteins in Biological Tissues.*" Biophy J 82, 493-508 (2002)). We thereby verified that the muscle fibers we imaged were almost exactly parallel to the face of the endoscope, thus permitting us to make accurate sarcomere length determinations by imaging in the two lateral spatial dimensions (Methods).

We next measured sarcomere lengths at different body positions. In the gastrocnemius of anesthetized mice (n=7), sarcomere lengths depended on the angle of the ankle, as shown in FIG. 6A, due to changes in total muscle length. Across mouse subjects, sarcomere lengths shortened from 3.15±0.06 (s.e.m) µm to 2.55±0.14 µm during changes in ankle angle from 70-170 degrees. This matches the operating range of 3.18-2.58 µm that we estimated based on a biomechanical analysis (Delp, S. L. et al., "*An Interactive Graphics-based Model of the Lower Extremity to Study Orthopedic Surgical Procedures.*" IEEE Trans Biomed Eng 37, 757-767 (1990)) using measurements of muscle length, pennation angle, moment arm length, and an assumed optimal sarcomere length of 2.8 µm for a 120° ankle angle.

We further used such microendoscopy to capture the dynamics of sarcomere contractions. Because these dynamics elapse over milliseconds, we performed laser line-scans at 200-1000 Hz perpendicularly across rows of sarcomeres undergoing changes in length. To induce muscle contraction in anesthetized mice, we electrically stimulated the gastrocnemius proximal to the site of microendoscopy (see Methods, supra). This triggered a contraction, which we visualized with ~1-3 ms time resolution (FIG. 6B). Across multiple mice (n=5) in which the microendoscope was inserted a similar distance from the ankle, mean sarcomere length was 3.05±0.02 (s.e.m) µm prior to stimulation and 2.55±0.03 µm afterwards (FIG. 6C). Mean contraction speed peaked at 8.00±0.05 (s.e.m) µm s$^{-1}$ during electrical stimulation (FIG. 6D), which is within the range of maximum fibers responding in vitro to a chemical stimulus.

To demonstrate the applicability of microendoscopy to studies and diagnostics in humans, we visualized individual sarcomeres within the extensor digitorum muscle of healthy human subjects (n=3). After placing a 20-gauge hypodermic tube into the extensor digitorum, we inserted a 350-µm-diameter microendoscope through the tube and into the muscle. The hypodermic was removed and the microendoscope held in place. The subject's arm was placed in a brace, immobilizing the forearm and wrist but leaving the fingers mobile. After commencing SHG imaging we are able to visualize sarcomeres and their length fluctuations. Motion artifacts were often substantial but were reduced by bracing the limb. This tactic does not eliminate artifacts due to involuntary muscle twitching, which could only be overcome by increasing the laser-scanning speed to 400-1000 Hz. Subjects were asked to move their fingers into fully flexed and extended positions. Systematic variations in sarcomere length between these two positions were evident from images across all subjects, but each person exhibited slightly different ranges of sarcomere operation. With fingers flexed, mean sarcomere lengths from three subjects were 3.15±0.03 µm, 3.30±0.01 µm and 3.25±0.05 µm (n=12, 17 and 11 trials, respectively); with fingers extended these values were 2.97±0.03 µm, 3.24±0.02 µm, 3.12±0.02 µm (n=10, 10, and 7 trials), illustrating our ability to determine how human sarcomere lengths depend on body posture. Subjects reported feeling only mild discomfort during imaging sessions due to insertion of the microendoscope, indicating a potential suitability for eventual use during routine diagnostics of human sarcomere function.

Growing evidence from tissue biopsies indicates sarcomere structure and lengths are altered in numerous neuromuscular disorders that result from mutations in sarcomeric proteins. Visualization of sarcomeres by microendoscopy can facilitate efforts to diagnose the severity of these conditions, monitor progression, and assess potential treatments. Other syndromes in which monitoring sarcomere lengths might inform treatment choices include geriatric muscle loss and contractures due to cerebral palsy or stroke (see Plotnikov, S. V. et al., "*Measurement of Muscle Disease by Quantitative Second-harmonic Generation Imaging,*" Journal of Biomedical Optics in press (2008), and Ponten, E., Gantelius, S. & Lieber, R. L., "*Intraoperative Muscle Measurements Reveal a Relationship Between Contracture Formation and Muscle Remodeling,*" Muscle Nerve 36, 47-54 (2007). Combined SHG and two-photon microendoscopy of sarcomere lengths and fluorescent sensors or proteins in mouse models of diseases is a scientific tool to aid in the understanding of muscle biology and pathophysiology. Intraoperative sarcomere imaging during orthopedic reconstructions or tendon transfer facilitates efforts by surgeons to identify and set optimal sarcomere operating ranges. By reducing reliance on unproven assumptions, such as regarding the distribution of sarcomere lengths, in vivo sarcomere measurements improve biomechanical models that inform the understanding of human motor performance and development of rehabilitation technology, robotics, and prosthetic devices. For further discussion in this regard, reference may be made to Lieber, R. L., Murray, W. M., Clark, D. L., Hentz, V. R. & Friden, J., "*Biomechanical Properties of the Brachioradialis Muscle: Implications for Surgical Tendon Transfer.*" J Hand Surg [Am] 30, 273-282 (2005), Delp, S. L. et al., "*OpenSim: Open-source Software to Create and Analyze Dynamic Simulations of Movement,*" IEEE Trans Biomed Eng 54, 1940-1950 (2007), and Manal, K., Gonzalez, R. V., Lloyd, D. G. & Buchanan, T. S., "*A Real-time EMG-driven Virtual Arm,*" Comput Biol Med 32, 25-36 (2002).

Optical degradation can occur when changing focal planes using a GRIN lens. In an example embodiment, a telecentricaly oriented GRIN endoscope is designed in a manner that allows a user of the endoscope to change the focal plane while maintaining constant power, maintaining and maximizing the resolution, and maintaining a constant magnification. The GRIN endoscope, which is a doublet consisting of a relay and objective lens, operates at infinite conjugates. In other words, collimated light, light whose rays are in parallel, in the endoscope is pivoted at the back aperture rather than focusing a point at the back of the GRIN lens. The focal plane of the GRIN endoscope of the instant embodiment can be changed by the user via an afocal focusing mechanism. The afocal focusing mechanism adds convergence or divergence to the normally collimated light and shifts the focal plane at the sample. This is opposed to translating a focusing lens to change the image planes. Further, in another example embodiment, the afocal mechanism is configured and arranged to keep the beam waist constant at the back aperture of the GRIN endoscope. Therefore, the power of the light delivered to the sample does not fluctuate during focusing. Further, the collimated light beam supplied to the GRIN endoscope can be provided such that the beam overfills the back aperture of the GRIN endoscope. In this manner, the endoscope delivers the maximum available resolution, irrespective of the instant focal plane of the endoscope.

Figure 7:
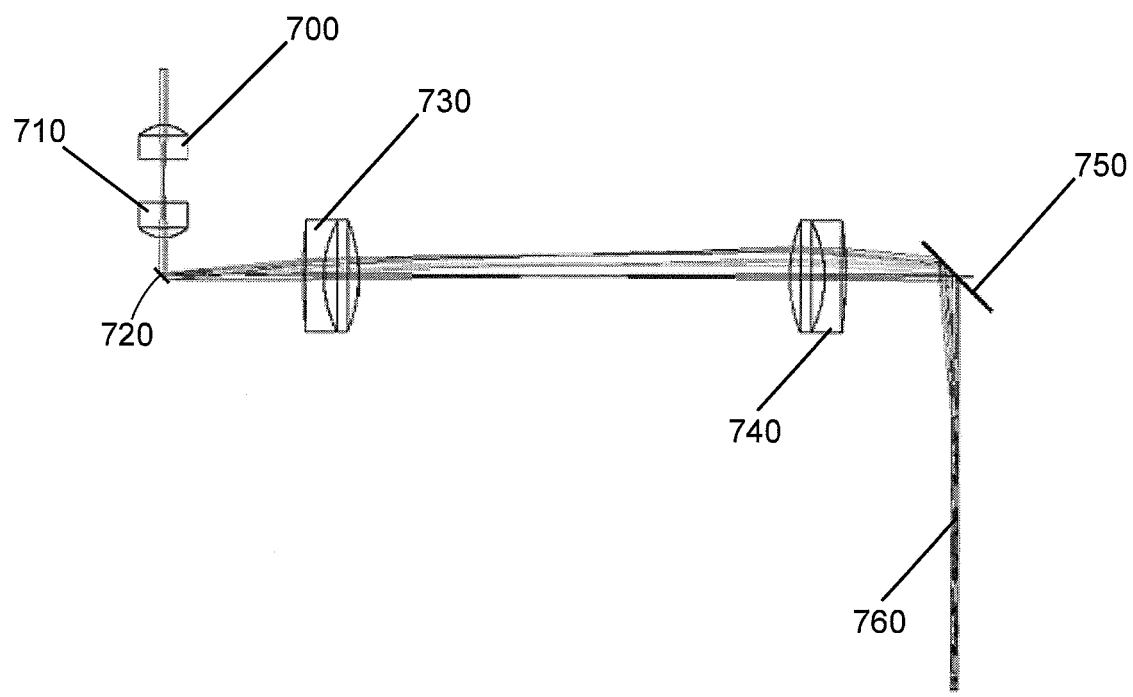
FIG. 7 is an optical pathway of a microscope, consistent with the instant disclosure.
Figure 8:
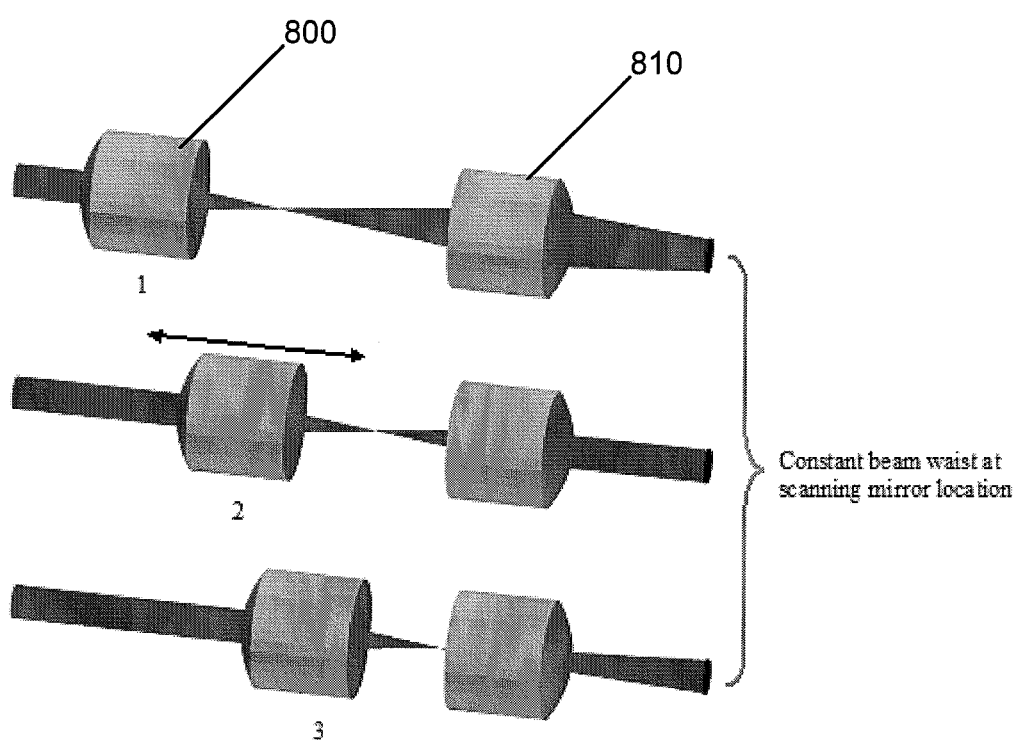
FIG. 8 shows a focus lens arrangement for three different image planes in an example embodiment consistent with the instant disclosure.

In the embodiments described herein, the focal plane of a GRIN endoscope accepting collimated light, and that delivers a focused spot at the sample's plane, can be altered by changing the shape of the incoming light beam. Turning now to FIG. 7, which shows a GRIN endoscope in accordance with an example embodiment of the instant disclosure. In an example embodiment, a pair of lenses 700/710 is arranged in an afocal arrangement. The pair of lenses 700/710 is used to change the shape of light beam provided to the GRIN endoscope 760. The example embodiment of the GRIN endoscope shown in FIG. 7 also includes a scan mirror 720, a scan lens 730, a tube lens 740, and a dichroic mirror 750. The lens closest to the scanning mirror 720 is fixed, the fixed focus lens 710, while the lens nearest the light source, the mobile focus lens 700, moves on an actuated stage. When the mobile focus lens 700 translates, the light beam diverges or converges depending on the direction the lens moved. The divergence and convergence of the light beam is shown in FIG. 8. FIG. 8 displays the focus lens arrangement for three different desired image planes. The left lens of the pair is the mobile focus lens 800, whereas the right lens is a fixed lens 810. The position of the lens shown at the top of FIG. 8, also labeled as position 1, is designed for shallow imaging (less than 100 µm). The position of the lens shown in the middle of FIG. 8, position 2, shows the neutral location where the outgoing beam is unaltered and yields a focal depth of 100 µm. The position shown in the bottom of FIG. 8, position 3, shows the lens arrangement designed for deeper imaging (greater than 100 µm). The mobile lens 800 can be placed at any location within its range, allowing the user to change the focal depth at the sample continuously between 0 and 150 µm. In each of the lens positions shown in FIG. 8, the exiting beam waist is constant within the focal plane of the fixed lens 810, regardless of the position of the mobile lens.

Turning again to FIG. 7 and also to FIG. 8, placing the scan mirror 720 in the focal plane of the fixed lens 710/810 provides a constant beam waist at the back aperture of the GRIN endoscope 760 because the scan lens 730 and tube lens 740 image the mirror to the same plane. Therefore, regardless of the position of the mobile lens 700/800, the intensity profile at the back aperture of the GRIN remains the same, and therefore power delivered to the sample remains constant. Further, in certain embodiments, the beam waist is sized so that it is slightly larger than the back aperture of the GRIN endoscope. As a result, the beam diameter stays fixed, and light overfills the GRIN endoscope, which delivers a maximum available resolution for all focal planes. Moreover, in certain embodiments, when the focal lengths of the two focusing lenses, the mobile focusing lens 700/800 and the fixed focusing lens 710/810, are different, this mechanism doubles as a beam expander/de-expander.

In FIGS. 9A-C, the resulting beam waist at the back aperture of the GRIN endoscope is shown for the same lens positioning in FIG. 8. FIG. 9A shows the beam waist of position 1 shown in FIG. 8. FIG. 9B shows the beam waist of position 2 shown in FIG. 8. FIG. 9C shows the beam waist of position 3 shown in FIG. 8. Also shown in FIGS. 9A-C is the tube lens 910 and the dichroic mirror 900, shown in the example embodiment of the GRIN arrangement in FIG. 7. In each of the arrangements, the diameter of the beam waist at the back of the GRIN endoscope 920 is constant. This keeps the power at the sample constant and the resolution at an optimal level for all focusing positions. Although the above embodiment is detailed with reference to a GRIN lens arrangement, the afocal focusing method described could be employed in any scanning microscope (e.g., laser scanning microscope) to change focus of the microscope without physically translating the objective.

The magnification of the GRIN endoscope can also change when shifting the focus to different planes. In certain instances, precise measurements require the user of an endoscope to record and track the instantaneous magnification, and correct for that factor in the measurement. This type of repeated scale corrections is an unnecessary hindrance, which can be eliminated using the telecentric lens arrangement describe in the instant embodiment.

"Telecentric" describes a lens arrangement whose chief rays exiting the GRIN endoscope objective are parallel to the optical axis. The parallel nature of the chief rays is independent of focus position, therefore, the size of the image plane remains constant apart from the depth that the probe is imaging.

The optical path through the GRIN endoscope of the instant embodiment is shown in FIG. 10A-B. A cutaway view of the back end of the GRIN endoscope is shown in FIG. 10A, where collimated light 1040 pivots near the back aperture of the relay lens 1000. A cutaway view of the front end of the GRIN endoscope is shown in FIG. 10B, highlighting the objective lens 1010, a 90° reflecting prism 1020 (modeled as a solid square of glass for simplicity), and a 100 µm thick layer of tissue 1030. In FIG. 10A-B the double dashed lines indicate the location of the cutaway. The relay lens 1000 consists of a half pitch multiple and therefore acts as a one-to-one imaging system, transmitting the pivoted collimated rays from its back aperture to its front aperture. The angle of the pivoted rays exiting the relay is identical to the incoming angle for even multiples of the half pitch length, and is reversed for odd multiples. The objective takes this light and focuses it to a point in the imaging plane. When the light entering the endoscope is pivoted, the focal point generated by the objective lens translates within the sample, making it possible to generate a scanned image. When the scanned light pivots at the front focal plane of the objective, the chief rays exit parallel to the optical axis, and there is no magnification effect that results from changing the focus position. In order to achieve the lack of magnification effect (interference), rather than pivot the light directly at the back aperture of the relay, the scan plane is shifted by a small amount (approximately 400 µm) relative to the back aperture of the relay lens. This shift makes the apparent scan plane reside at the front focal plane of the objective, and eliminates the magnification effect. Alternatively, the length of the relay lens itself can be altered to eliminate the magnification effect.

Figure 10:
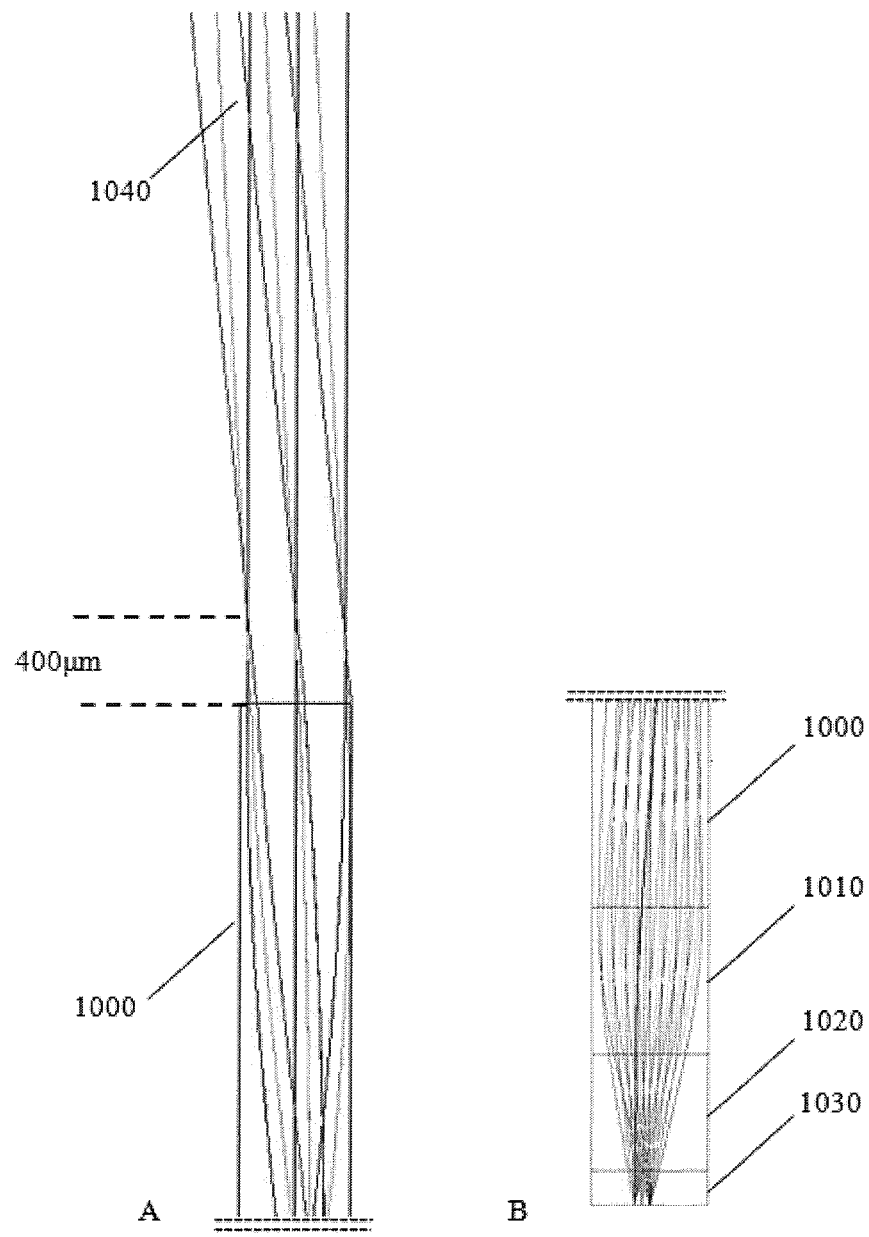
FIG. 10A shows beam scanning, consistent with an embodiment of the instant disclosure, at a location slightly above the back aperture of the GRIN endoscope relay.
FIG. 10B shows that the central "chief rays" of the same embodiment of FIG. 10A are parallel to the axis of the endoscope.

Also shown in FIG. 10 is a close up of the back of a GRIN endoscope in accordance with an example embodiment of the instant disclosure. Further, FIG. 10 shows where the pivoting of the beam takes place (approximately 400 µm above the surface of the relay lens 1000). This shifts the plane of scanning downstream so that the beam pivots at the front focal plane of the GRIN objective, shown in detail in FIG. 10B. The central "chief rays" of the different scanned angles are parallel to the axis of the endoscope, and therefore no magnification changes will result when shifting the focal plane.

Figure 11:
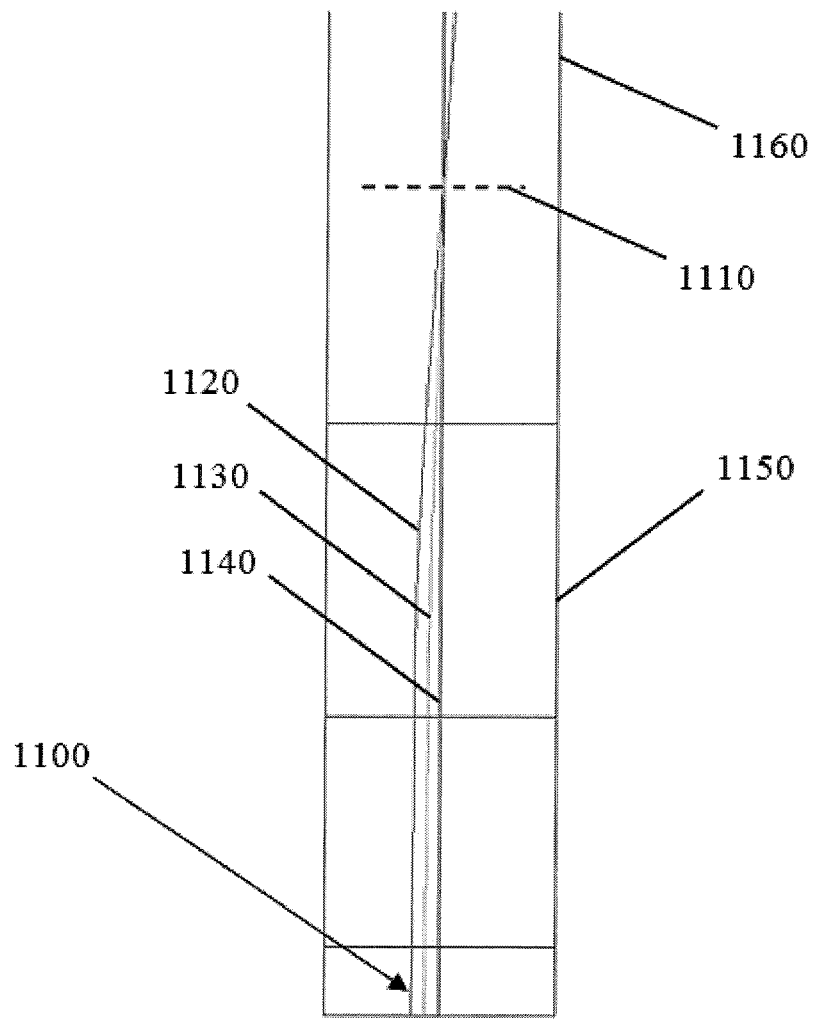
FIG. 11 shows only the chief rays of the same scan angles in FIG. 10.

The telecentric effect is further demonstrated in FIG. 11, which shows only the chief rays of the same scan angles from FIG. 10 to highlight the fact that they are parallel 1100 to the optical axis. Shown in FIG. 11 is the front focal plane 1110 of the objective 1150. FIG. 11 also shows the ray trace of the chief rays scanning at 0 degrees (1140), 1.5 degrees (1130) and 3 degrees (1120) at the scan mirror. All three are parallel to the center axis of the endoscope. Further, the pivot point of the chief rays occurs at the front focal plane 1110 of the objective 1150 which lies within the relay lens 1160.

Figure 12:
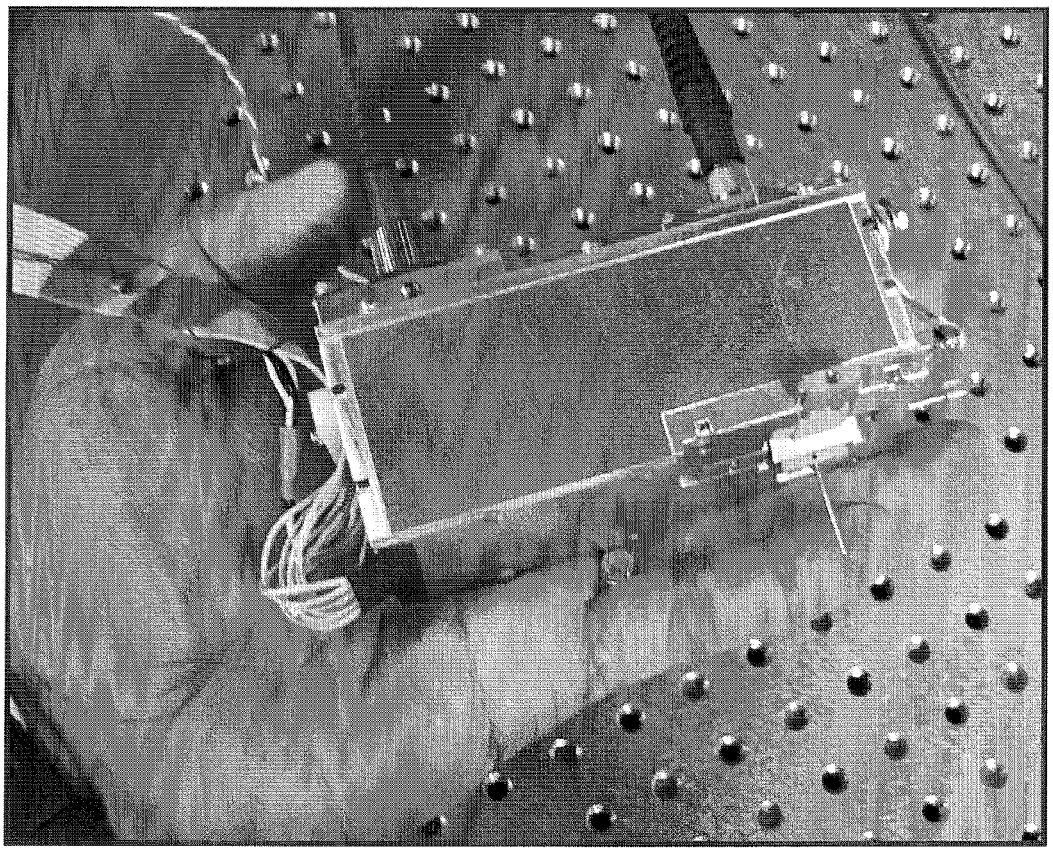
FIG. 12 shows an example machined handheld device and integrated endoscope, in accordance with the instant disclosure.

The GRIN optics with the telecentric arrangement, the afocal focusing mechanism, and the scan mirror and accompanying optics, can be incorporated into a single imaging system. An imaging system, consistent with the instant disclosure, is further described below. The description of the system is separated into two parts: description of a handheld device (HD), and description of an integrated endoscope (IE). When an HD is combined with an IE, scanning and signal collection necessary to generate images of deep tissue can be performed. An example embodiment of an IE connected with the HD is shown in FIG. 12.

Figure 13A:
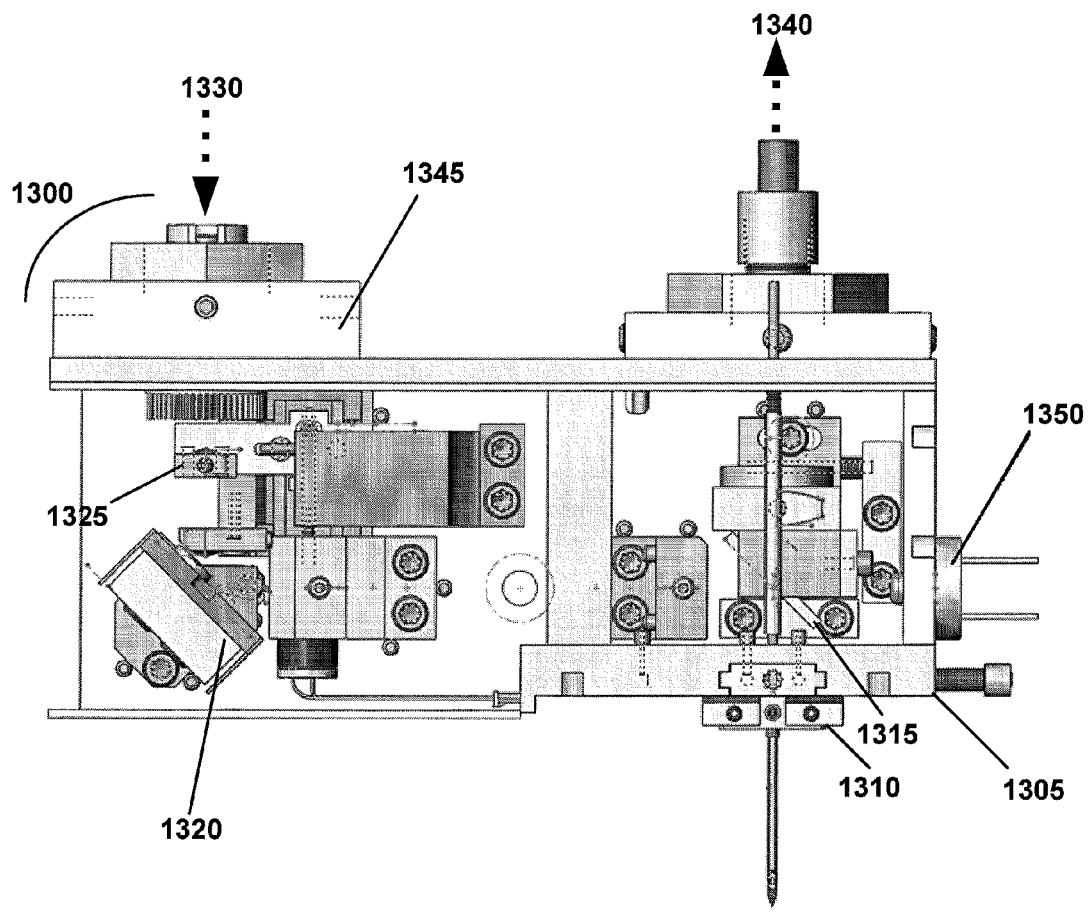
FIGS. 13A-B show example embodiments of a handheld device, and components thereof, consistent with the instant disclosure.

An example embodiment of a handheld device (HD) can be seen in FIG. 13A. Description of the HD will often include reference to an IE, which will be discussed subsequently in further detail. In the example embodiment shown in FIG. 13A, an HD 1300 is shown connected to an attached integrated endoscope (IE) 1310 via a precision clamping mechanism (PCU) 1305. Also included in this example HD 1300 is a collimating unit 1345, for collimating light 1330 provided to the HD. The light 1330 is delivered by a flexible, low dispersion fiber optic, most likely an air-core photonic chrystal fiber. Further, a focus stage 1325 is included to change the focal plane at the sample. The collimated and focused light then is provided to a MEMS scanning mirror 1320, as detailed above, which reflects the light towards a dichroic mirror 1315. The light is reflected by the dichroic mirror 1315 though an integrated endoscope (IE) 1310. The precision clamping mechanism (PCU) 1305, with translational adjustment, aligns the IE 1310 to the optical axis within the HD 1300 and to the scanning mirror plane.

Also included in the arrangement shown in FIG. 13A is an integrated power sensor 1350, which is aligned with the optical axis within the HD 1300. The integrated power sensor 1350 provides information regarding the alignment and functional status of the proceeding optical elements. The integrated power sensor 1350 can be calibrated to indicate the power delivered to the sample while imaging.

Figure 13B:
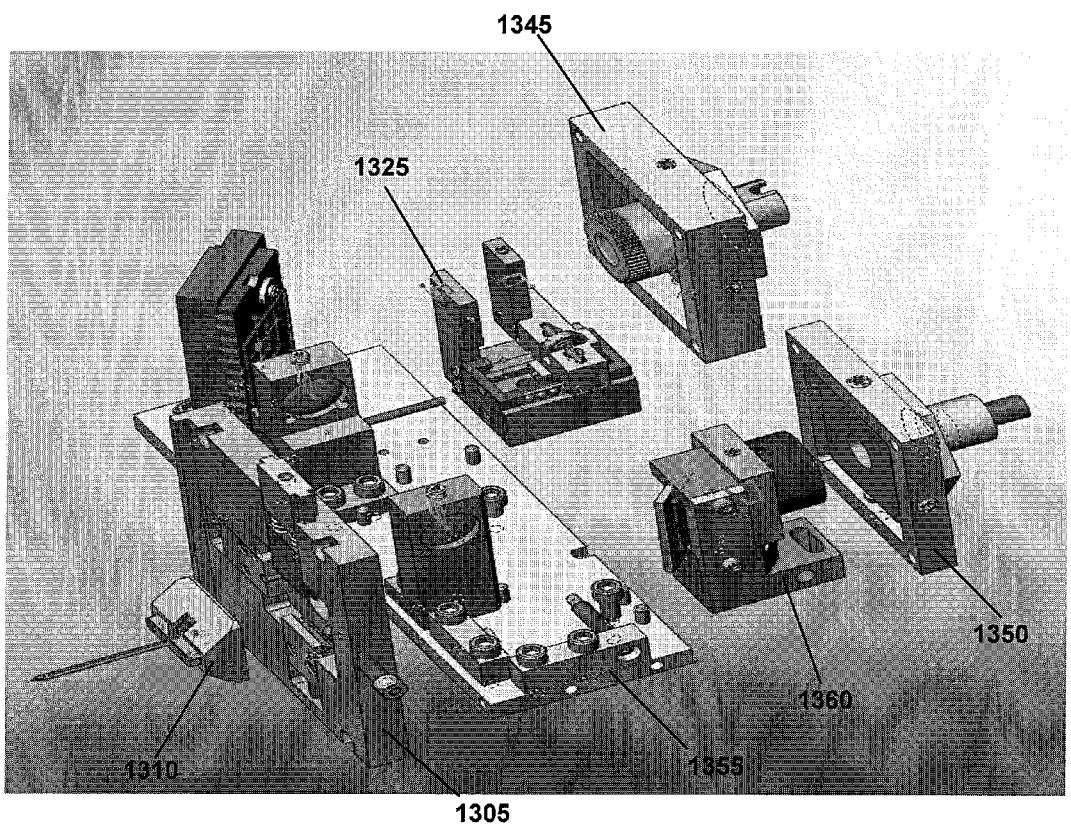

These components can also be seen in FIG. 13B, which shows the HD prior to integration of the components. The collimating unit 1345 of the HD is shown at the top of FIG. 13B. The collimating unit 1345 collimates light from a light source connected to the exterior of the unit. The collimated light would then pass through, assuming all the components of the HD are connected, the focusing unit 1325. A scanning unit 1355 provides a base for the MEMS mirror that reflects the collimated light towards the dichroic mirror, through the scan and tube lens (as described above with reference to telecentric focusing) and then towards the sample (as described above in FIG. 13A and further with reference to FIG. 14 below). Also shown in FIG. 13B are example embodiments of an integrated endoscope 1310, and a probe-clamping mechanism 1305, both discussed in further detail below. The collection unit 1360 is the component of the HD that both houses the dichroic mirror, directing light towards the sample, and additionally collects the light from the sample, and directs that light towards a signal fiber alignment unit 1350.

Figure 14:
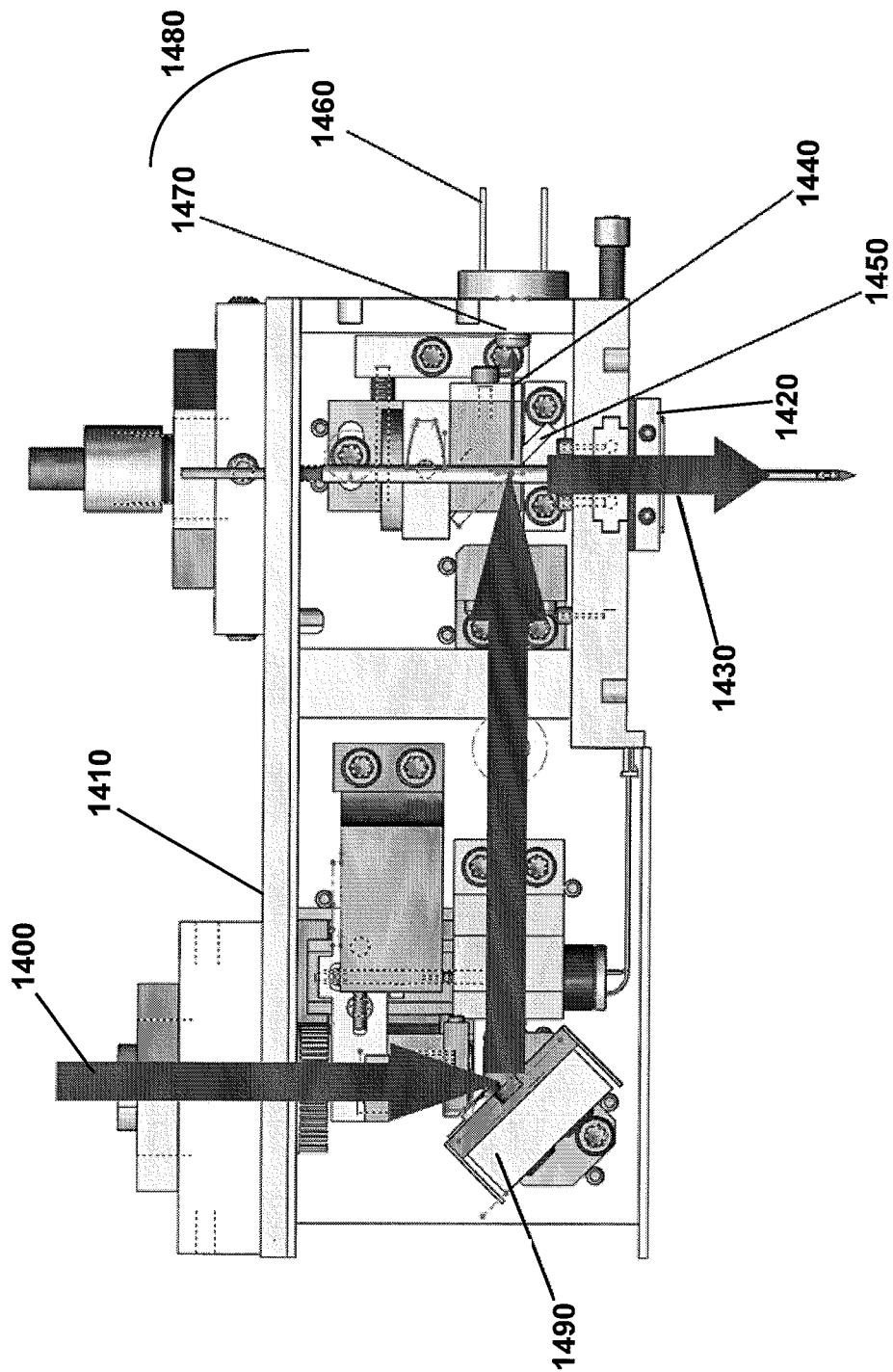
FIG. 14 shows a light path through an example embodiment of a handheld device, and the light paths relation to a photodiode for light power sensing.

Turning now to FIG. 14, which shows a light path through the HD, an integrated power sensor 1480 utilized in an HD 1410 can constantly measure the amount of optical power transmitted through the optical path 1400 of the HD 1410, as reflected off a MEMS mirror 1490 and provided to a dichroic mirror 1450, prior to entering the optics of the IE 1420. The integrated power sensor 1480 can be situated behind a dichroic mirror 1450 in and HD arrangement 1410. The integrated power sensor 1480 is configured to measure the approximately 1% of the excitation light, termed leakage light 1440, that leaks through the dichroic mirror 1450, and the remaining 99% of the light 1430 reaches the sample. The leakage light 1440 is directly proportional to the amount of light that is incident on the IE optics.

The integrated power sensor 1480 can consist of a photodiode 1470 in series with a fixed value resistor. When light falls on the sensor, the photons are converted by the photodiode 1470 into electric current, and by passing through the resistor, a voltage is generated that is proportional to the power of the incident light. The voltage measurement is provided via electrical leads 1460, and is monitored by, a highly sensitive multi-meter.

The integrated power sensor, as consistent with the instant disclosure, can provide valuable information during sample imaging. For example, the power sensor can indicate the functional status of all the proceeding components. The sensor reading is recorded at a benchmark power level after achieving optical alignment. When the reading at that same power level decreases either gradually or rapidly, the power change indicates that an optical element has been damaged, or has fallen out of alignment. Further, this indicator can be used to optimize the laser coupling into the delivery fiber because the indicator gives a direct reading of how much light is getting from the laser, through the fiber, and through the optics of the device. Moreover, the integrated power sample can be used as a real time indicator of the power delivered to the sample while imaging. After an IE is aligned to the HD, laser power is varied, and the power exiting the HD is correlated to the reading on the power sensor. Using these readings, the operator will have knowledge of how much power is present at the tip of the endoscope, and therefore prevent tissue damage from excessive laser power.

Figure 15A:
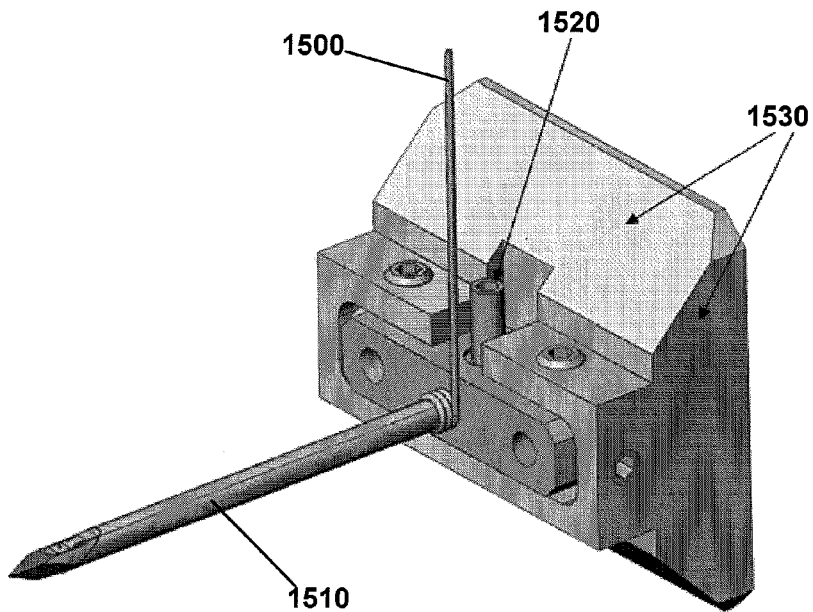
FIGS. 15A-B show example embodiments of an integrated endoscope in accordance with the instant disclosure.
Figure 15B:
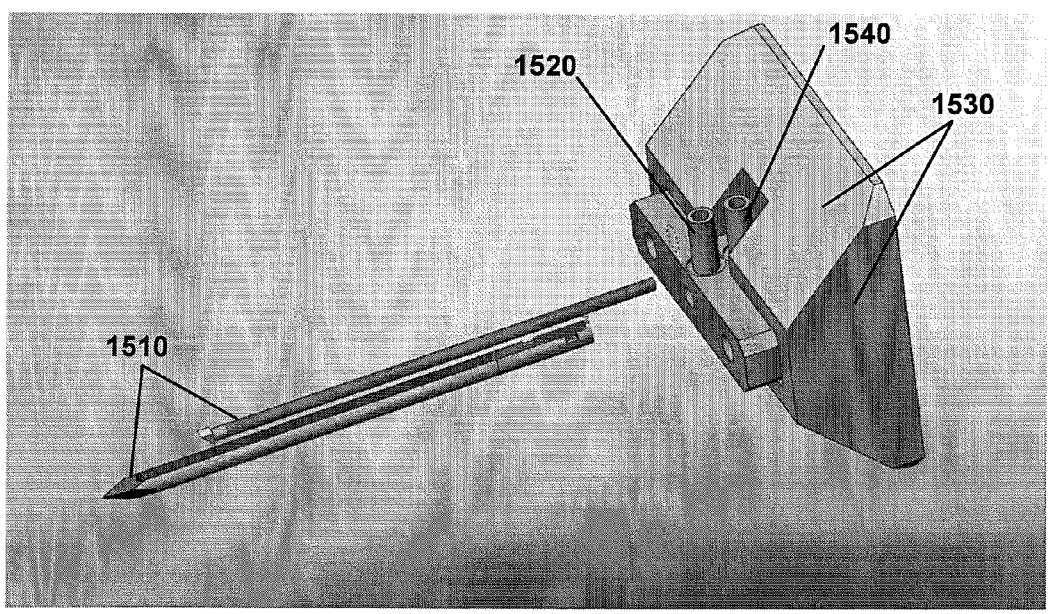

An integrated endoscope (IE) has been developed that allows for puncturing of thick tissue (e.g., muscle), and delivery of imaging optics in the same step. The IE has additional features that make it possible to collect both high quality static and dynamic images. The basic construction of the IE is seen in FIGS. 15A and 15B. The IE is composed of a GRIN based microendoscope and a rigid needle with a cutting point 1510; an outer insulating jacket, and a solid base that connects to a handheld device (as described in detail above). The IE also contains additional adjustment points to fine tune the alignment with the optical pathway (shown in further detail in FIGS. 23A-B and FIG. 24) within the HD. FIG. 15A also shows a wire for stimulation or sensing 1500, a part of the IE, that is connected to the needle with cutting tip and internal GRIN endoscope 1510. Further, the IE includes a suction port connection 1520 for blood removal. FIG. 15B shows an embodiment of the IE containing two ports: a blood removal suction port 1520, and a second port 1540 for providing a fluid to the sample. FIG. 15B additionally shows the separate elements of the needle 1510, which is described in further detail with reference to FIG. 16 and FIGS. 18-21.

Figure 16:
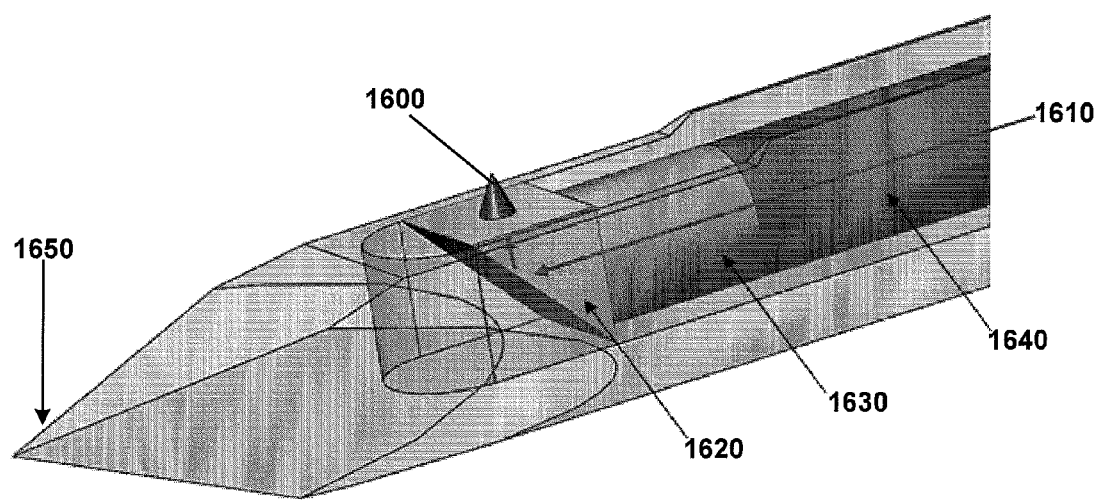
FIG. 16 shows a light path through a needle package and a GRIN-based endoscope in an example embodiment.

The microendoscope, described in detail above and shown again in FIG. 16, consists of a relay lens 1640, a more powerful objective lens 1630, and a 45-45-90 prism 1620. The prism allows for "side viewing" with the endoscope. The "side viewing" orientation provides multiple benefits. The tissue can be punctured directly with the IE itself. Additionally, there is no need for a separate delivery cannula. Furthermore, by translating the IE axially, it is possible to image different fibers within the same injection.

The endoscope cannot directly image along its axis due to the IE incorporating a needle with a solid point 1650. The needle 1650 is displayed transparently in FIG. 16 to facilitate visualization of the internal components and their spatial relationship to the needle. The prism 1620 bends the focused light from the objective 1630 out to the side of the IE. A laser light 1610 is provided through the endoscope, and passes through the GRIN relay 1640, and the GRIN objective 1630, where it is reflected by the prism 1620 and creates a focused spot 1600 outside of the IE. In this way, a sample positioned at the side of the IE can be visualized.

Figures 17A, 17B:
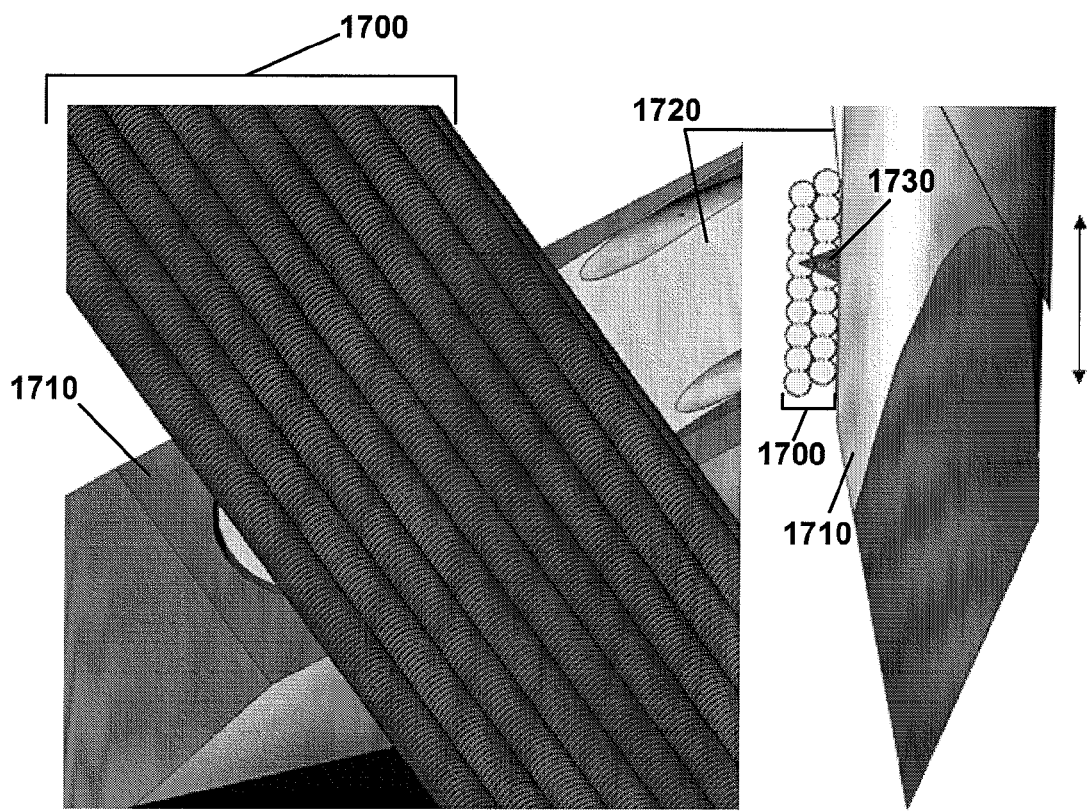
FIG. 17A shows an example imaging arrangement of the integrated endoscope relative to a set of muscle sarcomeres.
FIG. 17B shows a side view of the example imaging arrangement of FIG. 17A.

Turning now to FIGS. 17A and 17B, which show muscle fibers 1700 positioned along the side of the IE. The muscle fibers make contact with the outer surface of the IE 1720, putting them in direct contact with the imaging optics. In FIG. 17A, the striped pattern represents the sarcomere pattern 1700. The focus 1730 exiting the prism, or excitation cone, is perpendicular to the axis of the muscle fibers 1700. From the side, the focus 1730 is in the fibers near the periphery. Translating (indicated by the arrows in FIG. 17B) the needle 1710 within the hole allows direct imaging of separate fibers without the need for multiple injections.

Figure 18:
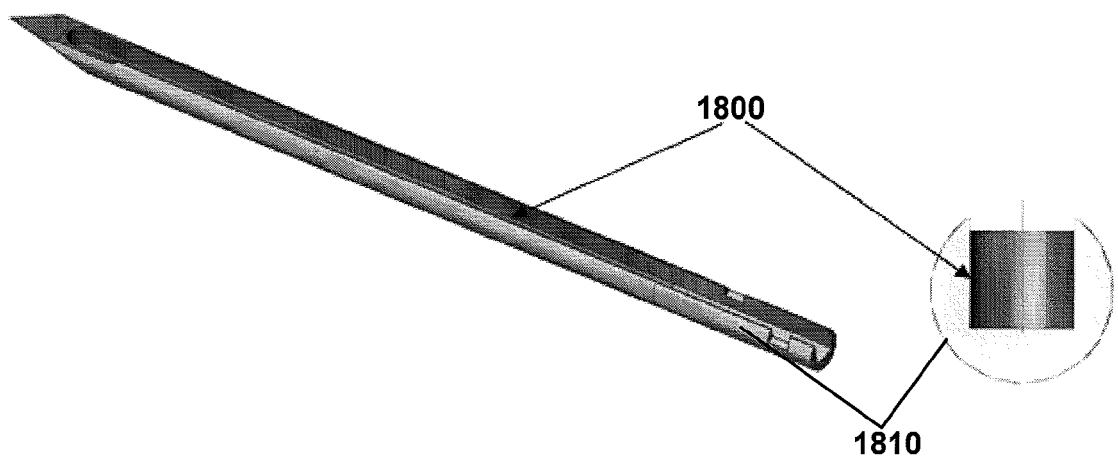
FIG. 18 shows a constructed needle, in accordance with the instant disclosure, having a pocket channel for GRIN optics.

Turning to FIG. 18, which shows an example needle 1810 that is used with the IE. The needle shown in FIG. 18 is machined out of a straight wire. A channel 1800 is cut along the axis of the wire that allows the GRIN optics to fit inside with the prism at the end of the channel, and flush to the perimeter. The needle 1810 has a solid tip (shown in detail in FIG. 19) which can be machined into a tri-facet trocar geometry, which is highly efficient at penetrating tissue. The three faces intersect at three edges which act like blades to slice through tissue. This arrangement helps ensure that the needle punctures the fascia that envelops the muscle, and also minimizes patient discomfort since there is less force needed to deliver the needle. The tri-facet trocar geometry can be replaced with an additional arrangement that minimizes damage or distortion of the sample at the injection site. In another example embodiment of the needle design, a hollow steel tube is used, as opposed to a manufactured wire, and a solid tip is attached. The solid tip can be manufactured into a cutting tip.

Figure 19:
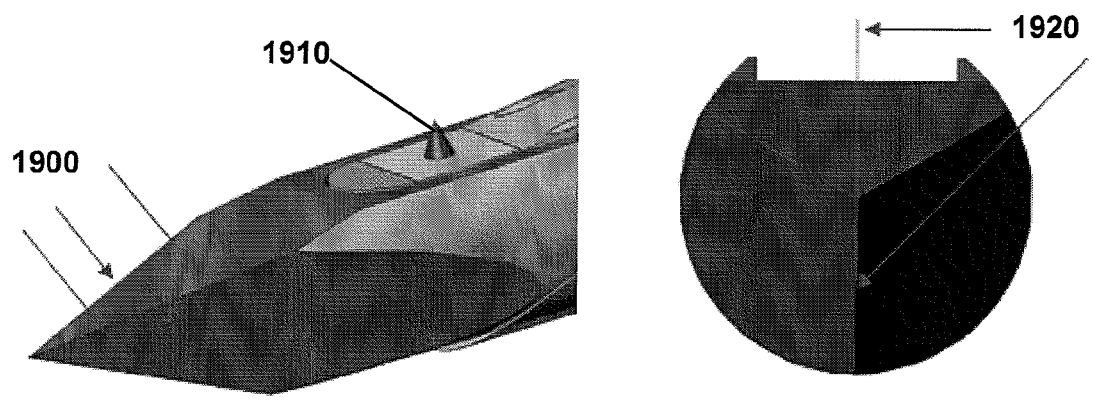
FIG. 19 shows a tri-facet geometry of an example embodiment of a needle.

Turning now to FIG. 19, this figure shows a detailed arrangement of the three faces of the needle 1900. The three faces of the needle 1900 intersect in a symmetric 120 degree pattern. The facets are aligned such that the cutting edge formed by the bottom two facets lies within the plane 1920 that bisects the optics channel. This orientation minimizes the likelihood that one of the cutting edges would slice the imaged muscle fibers. Instead, the muscle fibers will run along the flat face, and reach the prism intact. Images taken of punctured muscle verify that the fibers at the imaging site are not damaged. Other tip geometries could also be used for the solid tip. Also shown in FIG. 19 is the focused spot 1910 relative to the three faces of the needle 1900.

Figure 20:
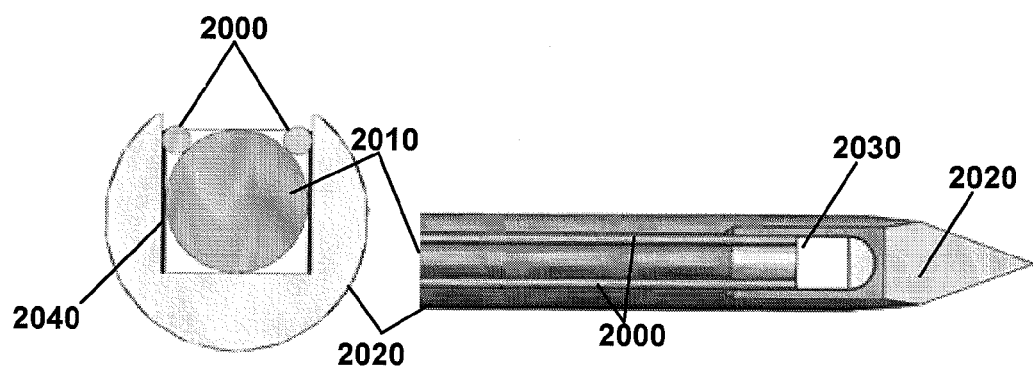
FIG. 20 shows suction line and GRIN optics placement in a needle in an example embodiment of the instant disclosure.

FIG. 20 shows suction line and GRIN optics placement in a needle in an example embodiment of the instant disclosure. The channel 2040 can be machined with a standard endmill, which produces an extruded rectangular pocket. The channel 2040 is large enough for the prism to fit inside, which means that the round cross sections of the GRIN lenses 2010 do not fully fill it. This provides an area where suction lines 2000 can be placed to remove blood. Additionally, the suction lines 2000 can be used for delivery of a liquid. For example, formulations can be injected to the imaging site to either aid with data collection, or to produce some other observable effect. The formulations can be a drug to reduce pain, clotting, to produce sustained contractions, or to inhibit contractions. In an example embodiment, the suction lines 2000 are cast into place using a medical device grade epoxy and Teflon® coated wires. The coated wires are placed in the gap between the GRIN endoscope 2010, and the side wall of the needle channel 2040. The coated wires run the length of the endoscope, and rest above the prism 2030 so that they exit the needle channel near the end 2020. When the endoscope is secured in place, epoxy fills the voids between the channel 2040 and the GRIN lenses 2010, and encapsulates the coated wires. Epoxy does not stick to the Teflon. Therefore, after the epoxy sets, the coated wires are removed, leaving a clean tube that runs the length of the IE, thus creating the suction lines 2000.

In certain embodiments, the suction lines are merged at a suction connector, therefore, both lines either provide suction or both deliver fluid. In other embodiments, the suction lines are independent of one another, therefore, one line could be used to inject saline, for example, while the other provides suction to clean the image site.

In an example embodiment, wires that are 100 µm in diameter are used. The holes at the top end of the IE can be plugged later, and a connector is secured to allow a small tube to connect to the IE, which draws blood out.

Figure 21:
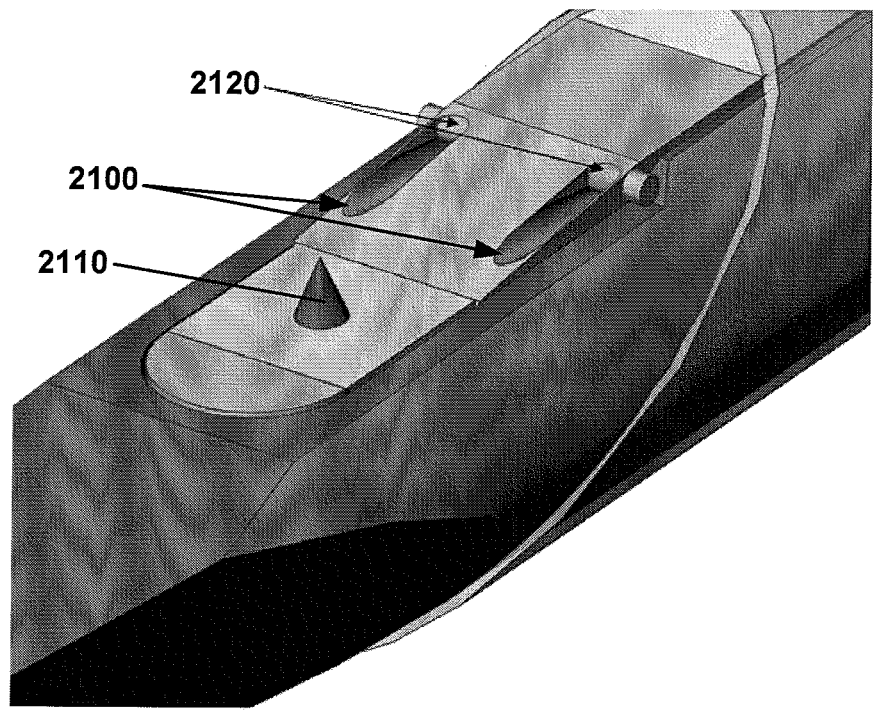
FIG. 21 shows suction inlet geometry of an example embodiment of the integrated endoscope.

Turning now to FIG. 21, a wire segment 2120 is attached at the end of the suction lines in order to avoid the suction lines coring out muscle tissue when the IE is injected. The smooth suction inlets 2100 are shown relative to the focused spot 2110. The smooth suction lines 2100 can be achieved, for example, by scraping by the epoxy until the wire 2120 is exposed, and polishing the arrangement clean. Tissue that contacts the inlets 2100 while the needle is being injected will run into the wire 2120, and slide over without coring because the wire 2120 is round and smooth. In another example embodiment, the wire segment is not used, and instead a geometry of the suction site that prevents coring is utilized.

Figure 22:
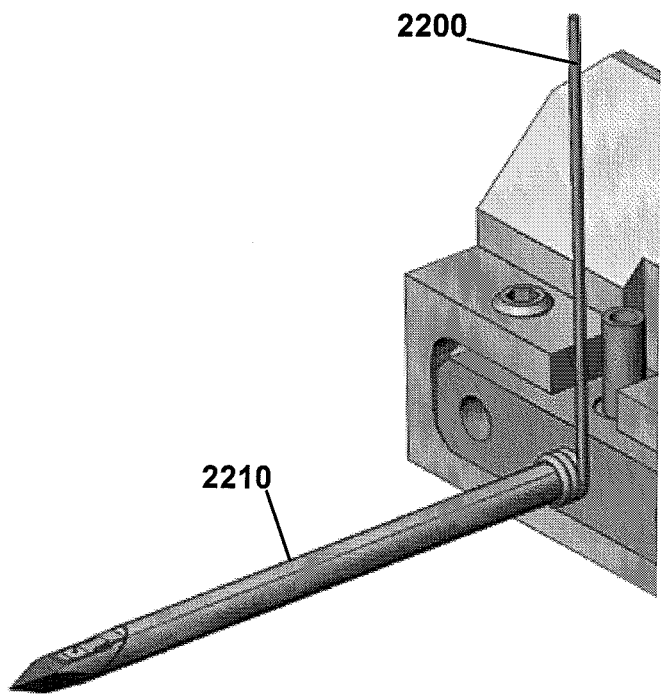
FIG. 22 shows a signal wire connected to a needle arrangement of an integrated endoscope in accordance with an example embodiment of the instant disclosure.

The needle-optics package is secured inside a polymer jacket that electrically insulates the endoscope. A wire is attached to the needle at the top of the IE that enables the user to monitor electric signals at the image site, or to apply a voltage to the muscle and illicit a local contraction. In FIG. 22, the outer jacket 2210 and the wire 2200 are shown near the base of the IE. The wire attaches to the base of the needle, so the tip of the IE is in electrical communication with this wire. In another example embodiment, the needle can have multiple, isolated conducting pathways that extend to the tip. Therefore, the needle can simultaneously excite contraction, and record electrical signals, or a differential method of measuring signals can be utilized.

Figures 23A, 23B:
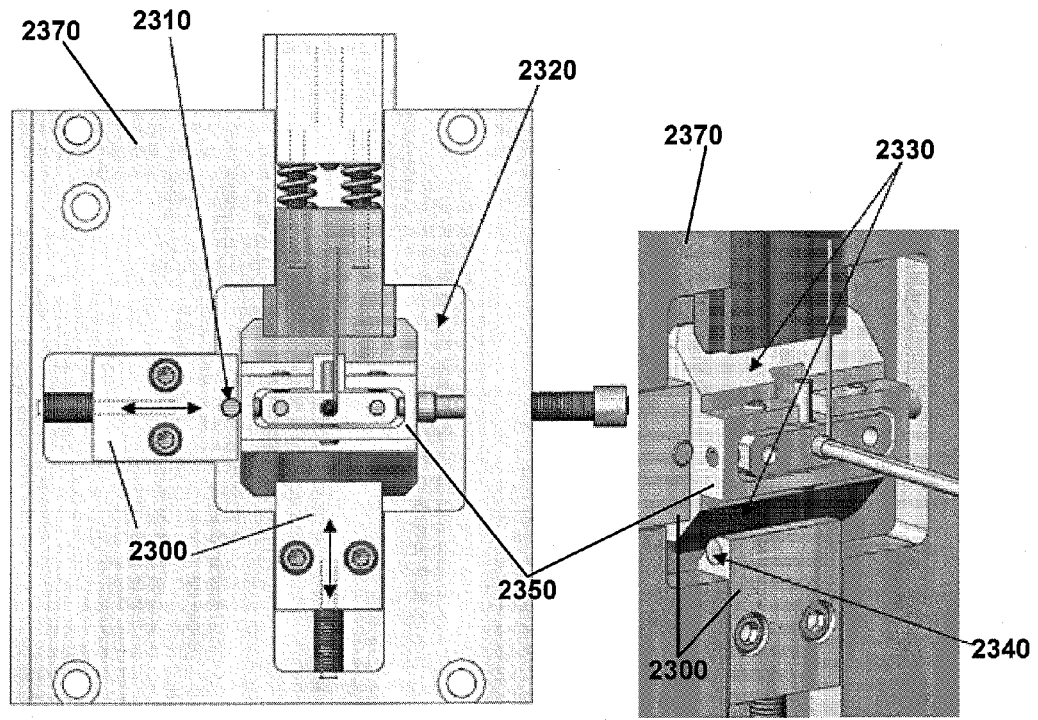
FIG. 23A shows an example probe clamping mechanism for securing an integrated endoscope to a handheld device based on the instant disclosure.
FIG. 23B shows a perspective view of FIG. 23A.

Incorporating a separate integrated endoscope (IE) into a small, all-in-one device, such as the handheld device (HD), is difficult due to the need for precise alignment of the optics. The alignment procedure of an IE and HD is described in detail with reference to the figures. Turning now to FIGS. 23A and 23B, the base of the IE is a large "button" 2350 that has a trapezoidal cross section. The button 2350 can be made out of brass or any acceptable metal substitute. The faces of the IE button 2350 are coupled to the clamping surfaces 2300 on the HD, and rigidly fix the IE to the Probe Clamp Unit body 2370. The "plane-line-point" clamping mechanism, described in further detail below, enables the IE to be taken on and off the HD, and return to the same clamped position with very high precision allowing for sterilizing the IE. The IE should first be aligned, and then autoclaved, as the IE should be autoclaved between uses. The clamps 2300 on the HD can be moved to provide coarse alignment of the IE to the optical path of the HD. In another example embodiment, the optics of the needle could be changed to have a selection of different IEs with different optical properties. Therefore, the "plane-line-point" clamping mechanism would allow the user to swap the different IEs with different optical properties in and out at will without the need for individual alignment.

This clamping mechanism is referred to as the Probe Clamp Unit (PCU). Proper position of the IE with the HD is important for maintaining optical alignment, which is directly related to the optical performance of the HD. The clamping strategy aims to locate the IE relative to the HD with particularity. A body in space has six degrees of freedom, and therefore can be fixed in a space by utilizing six points of constraint. A plane is defined by three points, a line by two, and a point by one yielding six points in total. FIGS. 23A and 23B show the PCU 2370 and an IE that is clamped in place.

The bottom of the button 2350 rests against the base plane 2320 of the PCU 2370. The base of the PCU acts as a planar constraint since it is machined flat. When clamped, the IE is constrained to translations within this plane. The line constraint exists in the form of a long pin 2340 that contacts one of the angled surfaces 2330 of the IE base. The long pin 2340 is held in one of the clamp jaws 2300, and contacts the 45 degree face 2330 on the button. This constrains the IE to translations along this line within the original plane. The flat side of the button 2350 contacts a vertical pin 2310 which constrains the IE to a point on the previously fixed line 2340, and therefore fully constrains the IE.

The function of the PCU is precision (not accuracy). In other words, the PCU mechanism positions an IE in a particular location, with a low level of variation, but the location is not unique. The clamped location of the IE can be changed by translating either of the constraint clamps 2300. Translating the constraint clamps alters the actual location of the clamped IE, but will not change the repeatability of the positioning in the new location. The translating constraint clamps can be utilized to adjust the optical alignment between the HD and the IE prior to imaging. The location of the laser beam within the HD can certainly deviate slightly from its ideal location. Therefore, when the laser beam reaches the IE, the optics within the IE may be slightly out of alignment. The moveable clamps 2300 on the PCU 2370 allow the IE to translate within the constraint plane, and maximize optical alignment.

Figure 24:
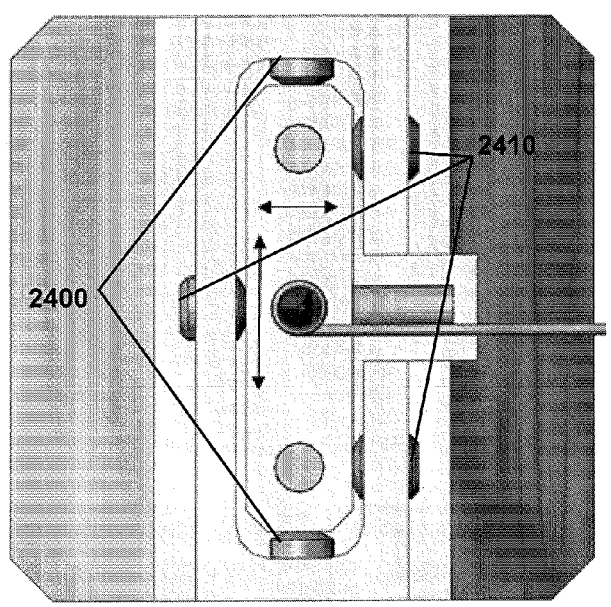
FIG. 24 shows an integrated endoscope alignment based on the instant disclosure.

To insure each individual probe is optimally aligned, the instant embodiment also allows for additional alignment freedom in the IE, because there is also variation within the IE itself. The base of the IE 2350 allows additional alignment of the optics within the needle to the optical path of the HD once the clamp positions are set. As shown in FIG. 24, the additional alignment can be accomplished by loosening and tightening the opposing pairs of set screws 2400/2410 to move the needle-endoscope portion of the IE within the pocket of the IE base. Once optimal alignment is achieved, the needle-endoscope portion of the IE can be fixed rigidly to the base. Different IEs can be swapped in and out of the HD in any given order without the need for additional alignment. This functionality allows for imaging multiple subjects quickly.

In order to ensure accurate alignment of the IE and the HD, an example clamping procedure of the IE and the PCU is provided. Turning to FIGS. 25A-D as a reference, a first clamping force is generated by the spring loaded block 2500. When engaged, the springs within this mechanism push an angled block 2505 against the IE base 2510, and generate a lateral and downward force that secures the IE relative to the HD.

The solid arrows of FIGS. 25A-D represent an applied forced in proportion to arrow size, and a dotted line indicates the translation of the components on which the dotted lines rest.

Figure 25:
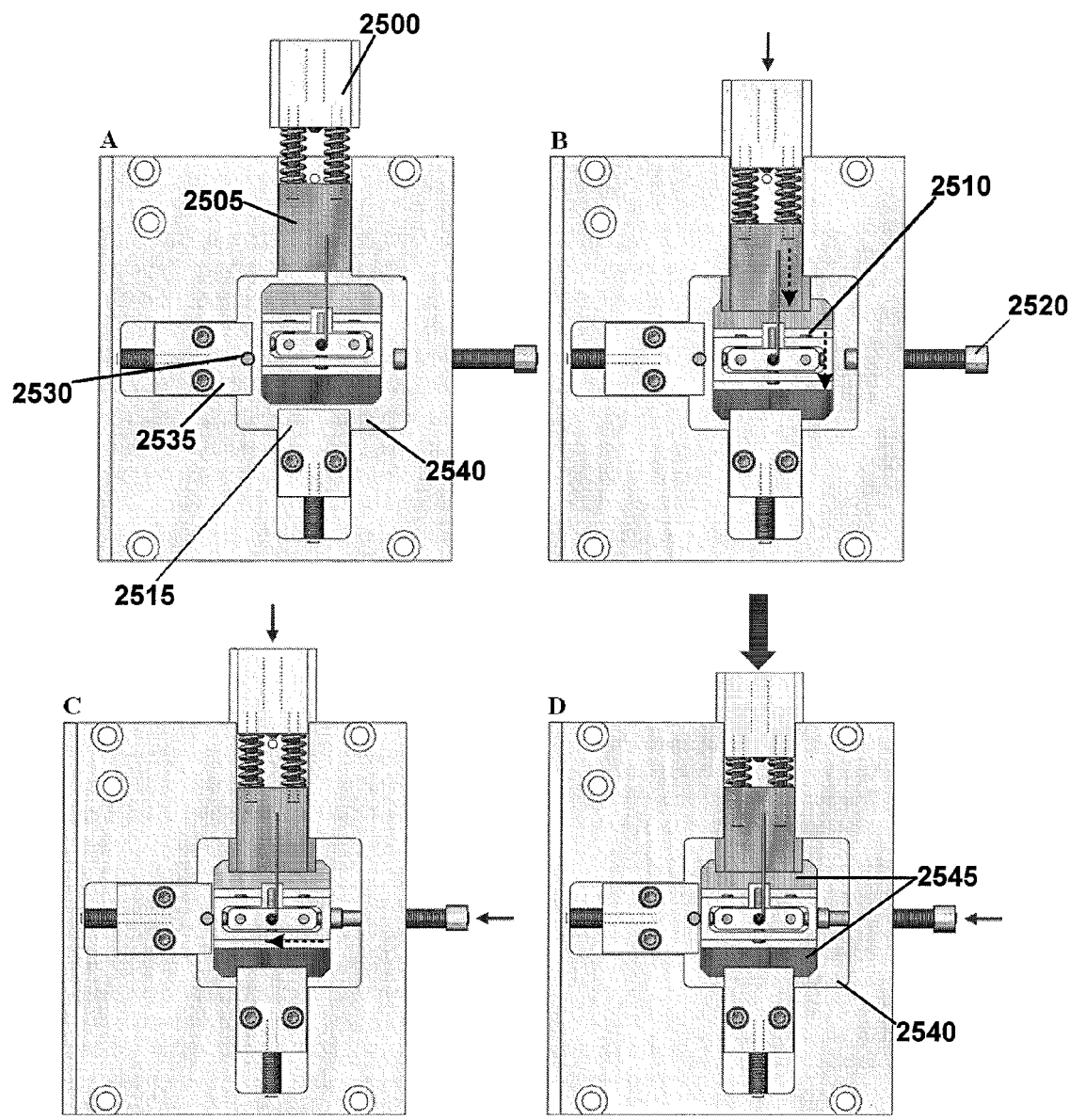
FIGS. 25A-D show an example procedure, in accordance with the instant disclosure, for clamping an integrated endoscope to a handheld device.

In order to secure the IE to the HD, turning to FIG. 25A, the spring loaded block 2500 is retracted to make space for the IE base 2510, and position the HD over the IE base 2510. As shown in FIG. 25B, gentle pressure should be applied on the spring loaded block 2500, which will squeeze the IE base 2510 between the line constraint pin 2515, and the angled portion 2505 of the spring loaded block 2500.

While maintaining pressure on the spring loaded block 2500, slight pressure is applied to a push rod 2520 to translate the IE base along the pin line until it contacts the point constraint 2530 on the opposing clamp 2535, as shown in FIGS. 25B-C. Turning to FIG. 25D by way of example, while continuing to maintain pressure on both the spring loaded block 2500 and the push rod 2520, the pressure on the spring loaded block 2500 should be increased. The increased pressure applied to the spring loaded block 2500 will compress the springs until a latch engages, and fixes the spring loaded block 2500 in place. The springs provide a consistent lateral clamping load that also pushes the IE base 2510 down into the PCU base 2540 due to the angled surfaces 2545 of the IE base 2510.

Figure 26:
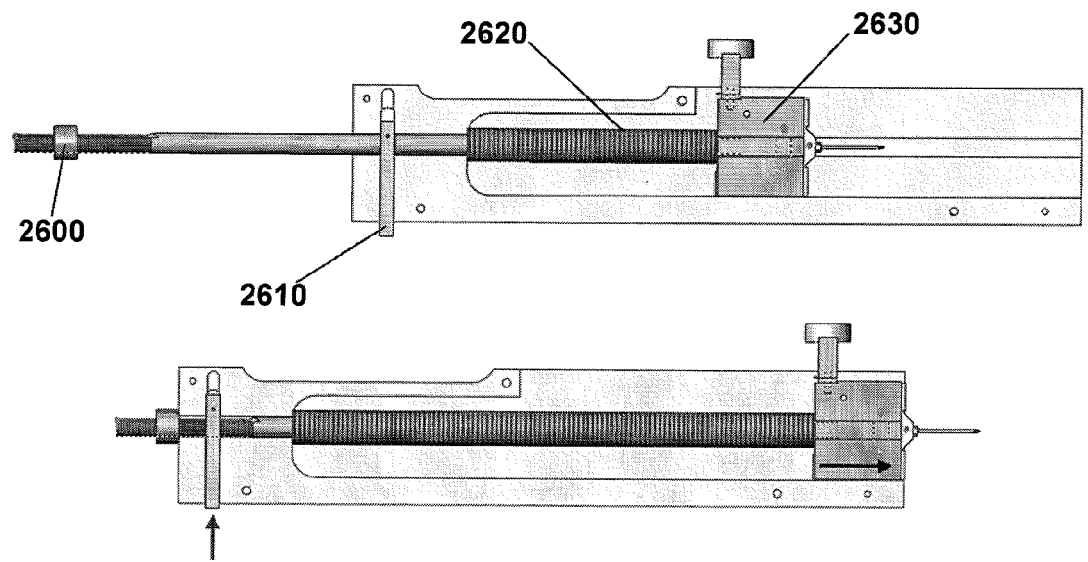
FIG. 26 shows a spring loaded trigger injector, in an example embodiment, that is used to deliver the integrated endoscope to a sample beneath the skin.

In certain embodiments of the instant disclosure, a rapid injector is provided to deliver the integrated endoscope (IE) to a sample (i.e., muscle) of interest beneath the skin. The use of an injector yields repeatable, clean, and less painful injections of the IE. As can be seen in FIG. 26, the injector consists of a spring 2620 loaded plunger that connects to the base of the IE prior to injection. A locking mechanism 2630 prevents the IE from accidentally shooting out of the injector. The locking mechanism 2630 can be a dual movement locking mechanism. Further, the injector includes a threaded portion on the end of the plunger with a stroke limiting block 2600 which makes it possible to adjust the depth of needle injection. A trigger 2610 is provided to release the spring 2620, and inject the needle.

Figure 27:
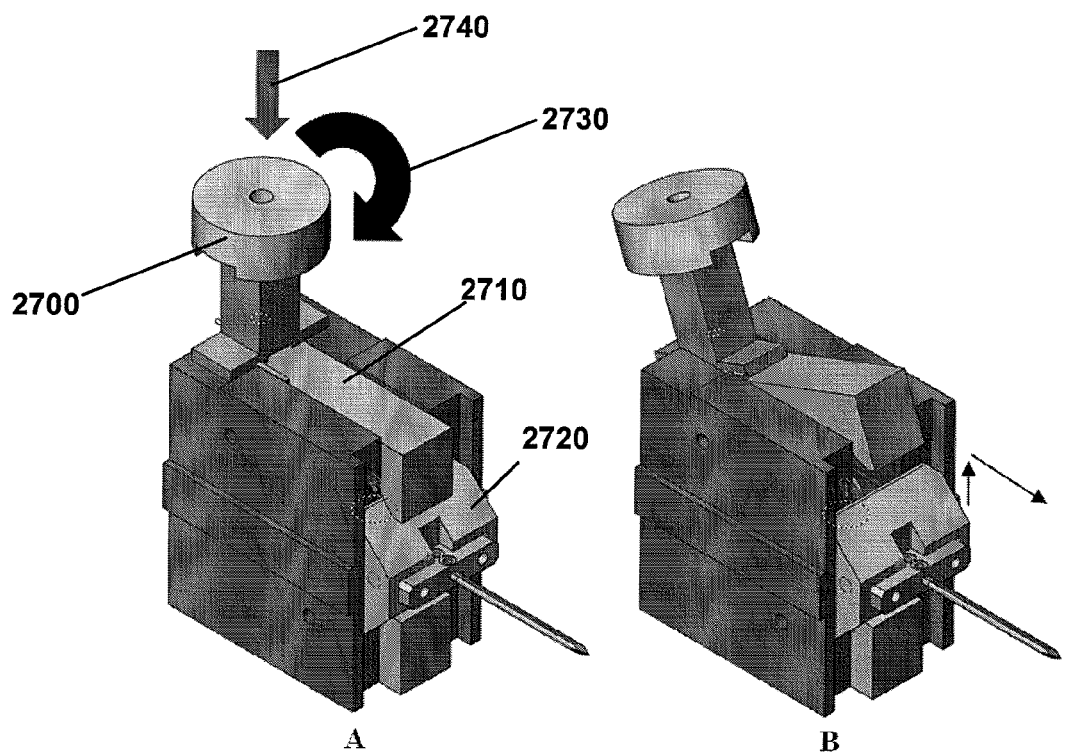
FIG. 27A-B show an example embodiment of a dual movement locking mechanism that prevents an integrated endoscope form being released from an injector.

FIG. 27 shows the dual locking mechanism in more detail. In the normal position, as shown in FIG. 27A, the base of the knob 2700 prevents the angled clamp 2710 from pivoting so the IE 2720 cannot be removed. FIG. 27B shows that the knob 2700 must be rotated clockwise 2730, and pushed down 2740, to pivot the angled clamp 2710 and release the IE 2720.

Figure 28A:
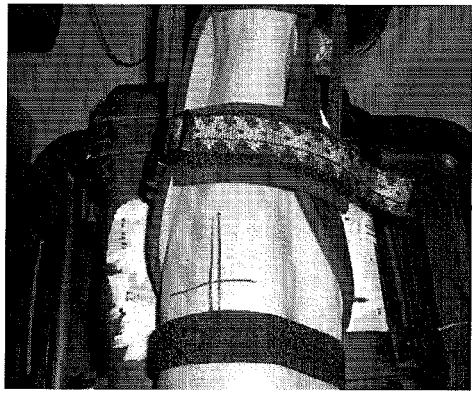
FIGS. 28A-C show an example procedure for attaching a handheld device and integrated endoscope, consistent with the instant disclosure; to a human subject.
Figure 28B:
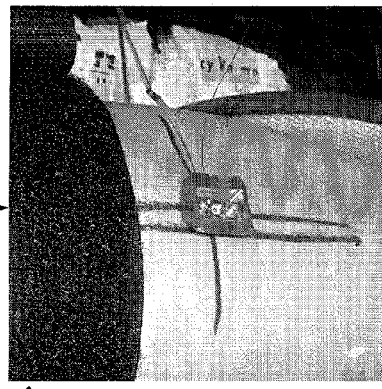
Figure 28C:
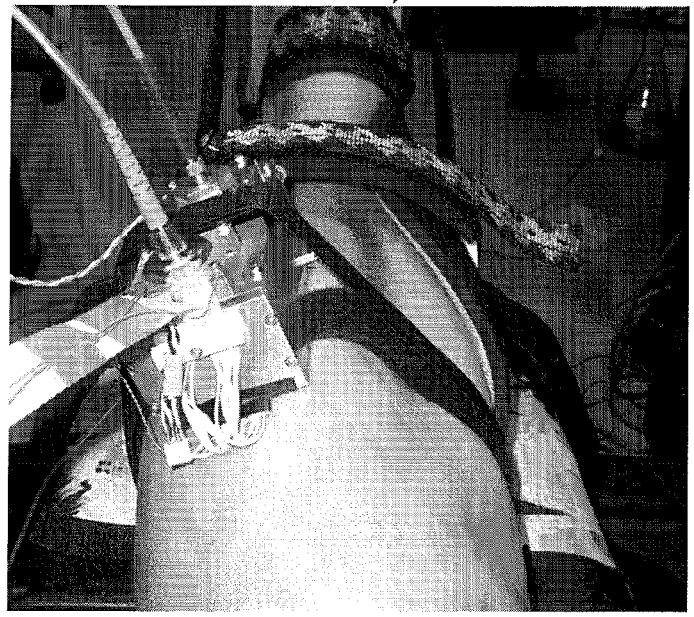

An example procedure for imaging a human muscle with a handheld device (HD), including an integrated endoscope (IE), can be seen with reference to FIG. 28A-C. An appendage of a human is first stabilized, and an area of interest is identified, FIG. 28A. A needle is inserted into the subject, FIG. 28B, and the handheld device, FIG. 28C, is attached and aligned (as described in detail above).

Figure 29:
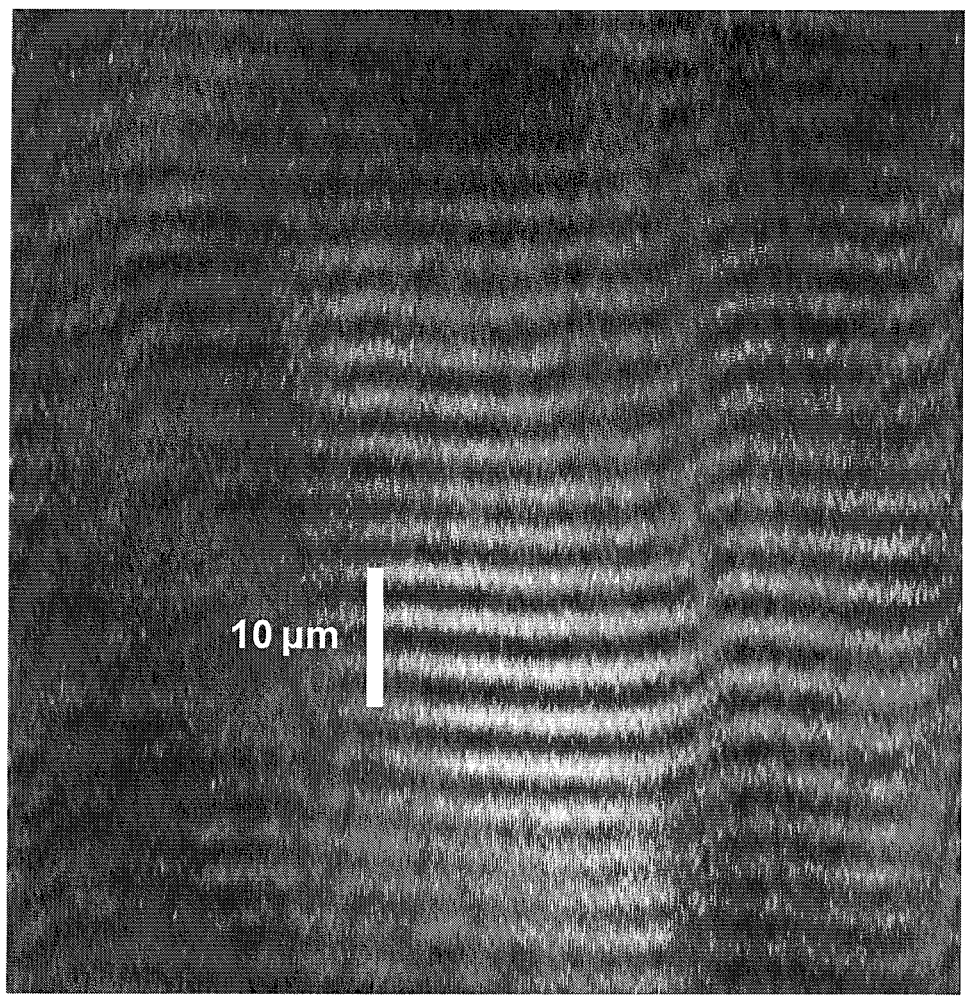
FIG. 29 shows an example muscle image achieved through use of a handheld device and integrated endoscope, consistent with the instant disclosure, of a tibialis anterior muscle of a human subject.

Clear muscle sarcomere images can be achieved through use of the attachment procedure. For example, a tibialis anterior muscle image is shown in FIG. 29.

In an example embodiment, consistent with the instance disclosure, a method is described for imaging an aspect of biological tissue, including muscle, via a light-delivering optical probe (in the biological tissue). The method is performed by using an objective, during focal plane changes, to focus the objective in the probe on the biological tissue while lessening adverse image-quality degradation. In certain specific embodiments, magnification effects are eliminated during focal plane changes. The method continues by using the optical probe to send light pulses toward structure in the biological thick tissue at a sufficiently fast line-resolution rate to mitigate motion artifacts due to physiological motion. In certain embodiments, the light pulses overfill the optical probe to deliver maximum resolution regardless of the focal plane changes, and in other embodiments, the light pulses provided to the optical probe are collimated and pivoted at a back aperture of the optical probe. Using the optical probe, as part of the method described, causes, in response to the light pulses, signals to be generated from and across a sufficient portion of the structure to span a sarcomere length. In using the probe select ones of the generated signals are collected, the signals are predominantly present due to properties intrinsic to the structure. As part of the method, data is provided in response to the collected signals. The data is used for high-resolution imaging of said portion of the tissue structure.

In certain specific embodiments of the method for imaging, the objective of the optical probe, used during focal plane changes, is characterized as telecentric. Further, magnification of the optical probe remains constant during focal plane changes. Moreover, in other specific embodiments of the method of imaging, constant power and maximum resolution of the light pulses are maintained during the focal plane changes. Constant power is maintained by providing the light-pulses with a constant beam waist. Maximum resolution is maintained by provided light-pulses to overfill a back aperture of the optical probe.

Another embodiment of the method uses an afocal lens arrangement to add convergence or divergence to the light pulses thereby shifting the focal plane at the biological thick tissue. In those embodiments utilizing an afocal lens arrangement, the afocal lens arrangement includes a mobile lens and a fixed lens. In other embodiments of this method, the light pulses provided to the optical probe are collimated and pivoted at a back aperture of the optical probe.

The instant disclosure is also directed towards an apparatus for imaging an aspect of biological tissue, which includes muscle. In certain embodiments, this apparatus can be used in a method of imaging an aspect of biological tissue (including muscle). The apparatus includes a light-delivering optical probe. The optical probe is configured and arranged with one end to be placed in the biological tissue. The light-delivering optical probe is further configured and arranged to send light pulses toward structure in the biological thick tissue at a sufficiently fast line-resolution rate to mitigate motion artifacts due to physiological motion. Moreover, the light-delivering optical probe is designed to cause, in response to the light pulses, signals to be generated from and across a sufficient portion of the structure to span a sarcomere length; and collect select ones of the generated signals that are predominantly present due to properties intrinsic to the structure. The apparatus additionally includes a telecentric objective and a collector. The telecentric objective in the light-delivering optical probe is designed to lessen adverse image-quality degradation during focal plane changes on the biological tissue by maintaining constant magnification during the focal plane changes. The collector is configured and arranged to provide data in response to the collected signals for high-resolution imaging of said portion of the tissue structure.

In certain specific embodiments of the apparatus, the optical probe further includes an afocal lens arrangement that is designed to maintain maximum resolution of the optical probe. In other specific embodiments, the optical probe can include an afocal lens arrangement configured and arranged to maintain constant power of the optical probe. The telecentric objective, in other embodiments of the apparatus for imaging an aspect of biological tissue, is designed to maintain constant magnification of the optical probe. In other embodiments, the apparatus also includes an afocal lens arrangement configured and arranged to provide convergence or divergence to the light pulses.

The instant disclosure also details a method for imaging an aspect of biological tissue, including muscle, via a light-delivering optical probe in the biological tissue. The method of the instant example embodiment is utilized by providing the optical probe with a needle, the optical probe and needle being integrated with an electro-mechanical end portion that is configured and arranged to puncture the tissue and while in the tissue, electro-optically access the biological tissue. In certain specific embodiments, the signals communicated between the electro-mechanical end portion and the biological tissue are those optically sensed for muscular contraction and/or for measuring the resulting sarcomere changes in response to electrically stimulating as another inventive aspect. Moreover, in other embodiments, the signals communicated between the electro-mechanical end portion and the biological tissue are to electrically stimulate. The method continues by using the optical probe to send light pulses toward structure in the biological thick tissue, and cause, in response to the light pulses, signals to be generated from and across a sufficient portion of the structure in the biological thick tissue to span a sarcomere length. Further, in response to signals communicated between the electro-mechanical end portion and the biological tissue, selected ones of the generated signals are collected, the generated signals are predominantly present due to properties in the structure. The method then operates by providing data in response to the collected signals for high-resolution imaging of said portion of the tissue structure.

In certain specific embodiments, the light pulses are sent toward structure in the biological thick tissue at a sufficiently fast line-resolution rate to mitigate motion artifacts due to physiological motion. Another embodiment of the method of imaging an aspect of biological tissue is further characterized in that the signals communicated between the electro-mechanical end portion and the biological tissue include signals which are electrically stimulating signals as well as the responsive optically sensible signals. Moreover, the responsive optically sensible signals are useful for detecting muscular contraction and/or for measuring the resulting sarcomere changes.

The needle of the optical probe used in the method can be, in certain embodiments, translated axially relative to tissue enabling multiple independent measurements from a single injection. Further, in other embodiments, the needle has differing optical properties for wide field or high resolution imaging.

The instant disclosure is also directed towards an optical imaging apparatus for imaging an aspect of biological tissue including muscle via an imaging-processing microscope and a light-delivering optical probe in the biological tissue. The optical imaging apparatus, in the example embodiment now described, includes an optical probe with a needle. The optical probe and needle are integrated with an end portion that is designed to puncture the tissue, and while in the tissue, electro-optically access the biological tissue. The optical imaging apparatus further includes an engageable clamp-mechanism interface. The engageable clamp-mechanism interface is configured and arranged to attach the optical probe with the imaging-processing microscope while maintaining optical alignment for imaging processing of the biological tissue.

Another embodiment of the instant disclosure is directed towards a method for imaging an aspect of biological tissue (including muscle) using a light-delivering optical probe having an objective. The method, of an example embodiment consistent with the instant disclosure, operates by providing a portable device for processing optical-signal data from the optical probe. Further, the method works by puncturing the tissue with the probe, and while in the tissue, collecting signals for high-resolution imaging of the tissue while lessening adverse image-quality degradation by controlling and maintaining power level and light-beam resolution for light pulsed through the light-delivering optical probe and objective. In certain specific embodiments, the portable device utilized in the method is hand-held.

The instant disclosure is also directed towards a method for imaging an aspect of biological tissue including muscle via a light-delivering optical probe having an objective. The method is characterized by puncturing the tissue with the probe, and while in the tissue, collecting signals for high-resolution imaging of the tissue while lessening adverse image-quality degradation by moving fluid near a biological-tissue image site for improving optical clarity via the objective. In certain specific embodiments of this method, moving fluid involves removing blood from the biological-tissue imaging site, and in other embodiments, moving fluid involves providing saline to the biological-tissue imaging site.

In certain specific embodiments, the method of imaging is further characterized in that the optical probe is used to send light pulses toward structure in the biological thick tissue at a sufficiently fast line-resolution rate to mitigate motion artifacts due to physiological motion; cause, in response to the light pulses, signals to be generated from and across a sufficient portion of the structure to span a sarcomere length; and collect selected ones of the generated signals that are predominantly present due to properties intrinsic to the structure. In this specific embodiment, the method provides data, in response to the collected signals, for high-resolution imaging of said portion of the tissue structure.

METHODS SUMMARY

Instrumentation.

In vivo imaging was performed on a laser-scanning microscope (Prairie) equipped with a wavelength-tunable Ti:Sapphire laser (Mai Tai, Spectra-Physics) and adapted to accommodate a microendoscope (see Jung, J. C. & Schnitzer, M. J., *"Multiphoton Endoscopy,"* Opt Lett 28, 902-904 (2003), and Jung, J. C. Mehta, A. D., Aksay, E., Stepnoski, R. & Schnitzer, M. J., *"In Vivo Mammalian Brain Imaging Using One- and Two-photon Fluorescence Microendoscopy,"* J Neurophysiol 92, 3121-3133 (2004). In most SHG studies, we used 920-nm-illumination. Epi-detected emission was band-pass filtered (ET460/50 m, Chroma). A 10×0.25 NA objective (Olympus, PlanN) focused illumination onto the microendoscope. Static images were acquired at 512×512 pixels with 8 µs pixel dwell time. Line-scans were 256-512 pixels long with 4 µs dwell time.

Animal Imaging.

After anesthetizing adult C57bl/6 mice, we placed a microendoscope inside or atop the muscle via a small skin incision. We used 1-mm- and 350-µm-diameter doublet microendoscopes (Grintech), respectively exhibiting 0.48 and 0.4 NA and 250-µm- and 300-µm-diameter working distances in water.

Human Imaging.

Under sterile conditions, a stainless steel clad 350-µm-diameter microendoscope was inserted into the proximal region of extensor digitorum via a 20-gauge hypodermic. We used a 350-µm-diameter microendoscope (Grintech) with a 1.75 pitch relay and a 0.15 pitch objective of 0.40 NA and 300-µm-working distance. In one situation, line-scan images were acquired at 488 Hz in the exterior digitorum muscle of a human subject with digits of the hand flexed and/or extended.

Data Analysis.

Mean sarcomere lengths in static and dynamic images were computed in Matlab (Mathworks) by calculating the autocorrelation across an image region that was one pixel wide and parallel to the muscle fiber's long axis. An $11^{th}$-order Butterworth band-pass filter selective for 1-5 µm periods was applied to the autocorrelation. Fitting a sine to the resultant yielded the dominant periodicity and mean sarcomere length. Analysis of length variations relied on measurement of individual sarcomere lengths performed at each pixel by finding distances between successive intensity peaks along a line parallel to the fiber's long axis. Locations of these peaks were found by fitting a one-dimensional Gaussian to each high-intensity region. A 2×5 pixel median filter, with its long axis aligned to the muscle fiber, smoothed the resultant image of sarcomere lengths.

METHODS

In Vitro Imaging.

Single muscle fibers were prepared by enzymatic dissociation of tibialis anterior from C57bl/6 mice using a method modified from Carroll et al. Tibialis anterior from a freshly sacrificed adult C57lb/6 mouse was incubated in 0.2% collagenase (Sigma, type IV) solution for 3-4 hours. After incubation, single fibers were obtained by trituration with a wide-mouth pipette, transferred to 90% Ringer's solution (in mM, 2.7 KCl, 1.2 $KH_2PO_4$, 0.5 $MgCl_2$, 138 NaCl, 8.1 $NaHPO_4$, 1.0 CaCl$_2$; pH 7.4) and 10% fetal bovine serum, and incubated for <1 day. The imaging system comprised a custom laser-scanning microscope equipped with a wavelength-tunable, ultrashort-pulsed Ti:Sapphire laser (Spectra-Physics, Mai Tai) and a 40× water 0.80 NA objective (Olympus, LUMPLFL). 720-nm-illumination was used to generate autofluorescence that was collected in the epi-direction and filtered with BG40 colored glass (Schott). 920-nm-illumination was used to generate SHG that was collected in the trans-direction by an identical 40× water microscope objective and filtered by an ET460/50 m filter (Chroma). In some experiments using SHG, the polarization of the laser light was varied with a half-wave plate to verify polarization dependence or to optimize signal intensity. Acquired images were four frame averages of 512×512 pixels using an 8 μs pixel dwell time.

Animal Imaging.

All animal procedures were approved by the Stanford Institutional Animal Care and Use Committee. Adult C57bl/6 mice were anesthetized by injection of ketamine (0.13 mg/g) and xylazine (0.01 mg/g i.p.). The hindlimb was shaved and fixed to a frame such that joint angles could be controlled. The imaging site was periodically irrigated with Ringer's solution. In experiments on sarcomere dynamics, we stimulated the muscle supra-maximally using a muscle stimulator (Medtronic, model 3128) with tungsten wires surrounding the proximal tibial nerve, which innervates the lateral gastrocnemius. We generally used either a 1-mm-diameter doublet microendoscope (Grintech, GmbH), composed of a 0.75 pitch Li-doped gradient refractive index (GRIN) relay lens of 0.2 NA coupled to a 0.22 pitch Ag-doped GRIN objective lens of 0.48 NA and 250-μm-working distance in water, or a stainless steel clad 350-μm-diameter doublet microendoscope (Grintech, GmbH), composed of a 1.75 pitch Li-doped GRIN relay lens of 0.2 NA coupled to a 0.15 pitch Ag-doped GRIN objective lens of 0.40 NA with a 300-μm-working distance in water. We performed laser line-scanning by first acquiring a reference image in two spatial dimensions and then choosing a linear path parallel to the long axis of the fiber for subsequent line-scanning.

Model of Sarcomere Length Versus Joint Angle.

The change in muscle-tendon length ($dl_{mt}$) with change in ankle joint rotation angle ($d\theta$) was determined using:

$$\frac{dl^{mt}}{d\theta} = ma,$$

where ma is the moment arm of the muscle. The moment arm and its variation with joint angle were determined by calculating the distance to the joint's center of rotation along the direction normal to the muscle's line of action. We calculated the change in muscle fiber length ($dl^m$) with change in ankle angle during passive motion by assuming that tendon stretch was negligible and thus:

$$\frac{dl^m}{d\theta} = ma(\cos\alpha),$$

where a is the pennation angle of the muscle fibers. Once the change in muscle fiber length with ankle angle was computed, the change in sarcomere length ($dl^s$) with joint angle (FIG. 3) was estimated using:

$$\frac{dl^s}{d\theta} = ma\cos\alpha(l_o^s/l_o^m)$$

where the optimal muscle fiber length ($l_o^m$) was determined by measuring the fiber length at the resting joint angle. The sarcomere length at the optimal fiber length ($l_o^s$) was assumed to be 2.8 μm.

Human Imaging.

All human imaging procedures were performed in accordance with FDA guidelines for the protection of human subjects (21 CFR 50) and approved by the Stanford Institutional Review Board. Subjects' forearms were restrained in a brace and fixed to the microscope's vibration-isolation table. All optical components were identical to those used during animal studies. However, all components, including microendoscopes and mounting components, contacting or potentially contacting human subjects at the imaging site were sterilized by autoclaving. After insertion of the microendoscope, subjects were asked to flex and extend their fingers and changes in sarcomere length were monitored. Duration of testing was <60 minutes in all cases.

Data Analysis.

Band-pass filtered images of sarcomeres were computed from raw images by applying an $11^{th}$-order Butterworth filter that acts as a band-pass for spatial periods between 1-5 μm. All analyzed images contained between 20 and 50 sarcomeres. For each muscle fiber, average sarcomere length was determined along each of a series of parallel lines aligned with the axis of the fiber. We report the mean and s.e.m. of this collection of measurements. Determinations of accuracy in average sarcomere length measured along a single line used the 95% confidence interval generated by a nonlinear least-squares curve fitting algorithm (Trust-Region algorithm, non-linear least-squares method). All data analysis was done in Matlab (Mathworks).

Assessment of Sarcomere Visibility.

The intensities of epi-detected SHG and autofluorescence signals are influenced by several wavelength-dependent processes, including attenuation of illumination in thick tissue, generation of signal photons at the focal plane, scattering of signal photons, and attenuation of signal photons within the detection pathway. Both the spatial arrangement and the contrast ratio between the maximum and minimum signal intensities observed within individual sarcomeres also influence sarcomere visibility. After exploring the illumination wavelength range of 720-980 nm using our tunable Ti:Sapphire laser, we found that given this light source and the transmittance characteristics of our microscope, SHG imaging with illumination of ~920 nm was most effective at revealing sarcomeres in vitro. We do not claim that 920 nm is the optimum excitation wavelength for imaging sarcomeres in thick muscle tissue, but rather that SHG imaging with 920-nm-illumination permits characterization of sarcomere lengths and dynamics in live subjects.

Potential Measurement Errors.

To minimize chances of photo-damage during imaging we maintained incident laser illumination below 30 mW, a reported approximate threshold for tissue damage. We also monitored for any physical signs of damage in the tissue. If a component of a muscle fiber or its lateral inter-fiber connections were substantially damaged, one might expect to see punctate, local differences in sarcomere structure distinct from surrounding tissue. We did not observe such effects, but rather observed sarcomeres with relatively uniform and smoothly varying lengths. We also performed control studies in which we tested quantitatively for any differences in sarcomere lengths between paired measurements obtained just prior to and then immediately after insertion of the microendoscope into the muscle. Prior to insertion we measured sarcomere lengths in the unperturbed muscle using an air objective (Olympus, 20×, 0.4 NA, LMPlanFL). We then inserted a microendoscope into the same tissue site and measured sarcomere lengths again. Comparison of the paired data sets revealed that sarcomere length determinations were virtually identical under the two conditions, differing by only 3.8±2.4% (mean±s.d.; n=45 measurement sites) and thereby precluding any substantial errors due to microendoscope insertion.

Another potential source of measurement error is parallax due to misalignment of the microendoscope's optical axis relative to the muscle fibers' transverse planes. However, a measurement error of just 1% would require a misalignment of over 8 deg, which was not observed in our three-dimensional data sets acquired with the microendoscope placed atop the muscle. In the mouse lateral gastrocnemius we found that muscle fibers were nearly parallel to the face of the microendoscope. From three-dimensional image sticks we measured an average misalignment of 3.3±1.8 deg (mean±s.d.; n=37 measurements from 4 stacks acquired in 4 mice). Such consistent mechanical alignment probably results in part due to pressure from the microendoscope on the muscle fibers. We conclude that in the lateral gastrocnemius measurement errors due to orientational misalignment are usually negligible. Similarly, misalignment errors seem likely to be minor in muscles in which the fibers lie parallel to the surface of the muscle, but perhaps less so in muscles in which the fibers vary significantly from this orientation.

For discussion relating to the above embodiments, reference may be made to the appendix document (Appendix A) filed in the underlying provisional patent application and entitled, "Direct Observation Of Mammalian Sarcomere Extension In Skeletal Muscle Using Minimally Invasive Optical Microendoscopy." This appendix document and all other patent and non-patent documents cited herein are incorporated by reference, each in its entirety.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. As an example, technology other than GRIN-lens technology may be used in implementing the microendoscopes discussed above. As another example, the above-described methods and arrangements for using lead channels having multiple optic probes are applicable to both skeletal sarcomere and cardiac sarcomere. Such modifications and changes do not depart from the true spirit and scope of the present invention, which is set forth in the following claims.

What is claimed is:

1. A method for imaging an aspect of biological tissue including muscle via a light-delivering optical probe in the biological tissue, the method comprising:
    using an objective during focal plane changes to focus the objective in the probe on the biological tissue while lessening adverse image-quality degradation;
    using the optical probe to
        send light pulses toward structure in the biological tissue at a sufficiently fast line-resolution rate to mitigate motion artifacts due to physiological motion,
        cause, in response to the light pulses, signals to be generated from and across a sufficient portion of the structure to span a sarcomere length,
        collect select ones of the generated signals that are predominantly present due to properties intrinsic to the structure; and
    providing data in response to the collected signals for high-resolution imaging of said portion of the tissue structure.

2. The method of claim 1, wherein the objective is telecentric and maintains constant magnification during the focal plane changes.

3. The method of claim 2, wherein the telecentric objective maintains constant magnification of the optical probe.

4. The method of claim 1, wherein the method further includes maintaining maximum resolution of the optical probe during the focal plane changes by providing the light pulses to overfill a back aperture of the optical probe.

5. The method of claim 1, wherein the method further includes maintaining constant power of the optical probe during the focal plane changes by providing the light pulses with a constant beam waist.

6. The method of claim 1, further comprising using an afocal lens arrangement to maintain power of the light pulses.

7. The method of claim 1, further comprising using an afocal lens arrangement to provide convergence or divergence to the light pulses, thereby shifting the focal plane at the biological tissue.

8. The method of claim 7, wherein the afocal lens arrangement includes a mobile lens and a fixed lens.

9. The method of claim 1, wherein the light pulses provided to the optical probe are collimated and pivoted at a back aperture of the optical probe.

10. The method of claim 1, wherein the optical probe includes an afocal lens arrangement that maintains maximum resolution of the optical probe.

11. The method of claim 1, wherein the optical probe includes an afocal lens arrangement that maintains constant power of the optical probe.

12. The method of claim 1, further including using an afocal lens arrangement to provide convergence or divergence to the light pulses.

13. A method for imaging an aspect of biological tissue including muscle via a light-delivering optical probe in the biological tissue, the method comprising:
    providing the optical probe with a needle, the optical probe and needle being integrated with an electro-mechanical end portion that is configured and arranged to puncture the tissue and while in the tissue, electro-optically access the biological tissue;
    using the optical probe to
        send light pulses toward structure in the biological tissue,
        cause, in response to the light pulses, signals to be generated from and across a sufficient portion of the structure in the biological tissue to span a sarcomere length,
        in response to signals communicated between the electro-mechanical end portion and the biological tissue, collect selected ones of the generated signals that are predominantly present due to properties in the structure; and
    providing data in response to the collected signals for high-resolution imaging of said portion of the tissue structure.

14. The method of claim 13, wherein the light pulses are sent toward structure in the biological tissue at a sufficiently fast line-resolution rate to mitigate motion artifacts due to physiological motion.

15. The method of claim 13, wherein the signals communicated between the electro-mechanical end portion and the biological tissue are sensed for muscular contraction.

16. The method of claim 13, wherein the signals communicated between the electro-mechanical end portion and the biological tissue are the resulting sarcomere changes in response to an additional step of electrically stimulating the biological tissue.

17. The method of claim 13, wherein the signals communicated between the electro-mechanical end portion and the biological tissue are to electrically stimulate.

18. The method of claim 13, wherein the signals communicated between the electro-mechanical end portion and the biological tissue include signals which are electrically stimulating signals as well as responsive optically sensible signals.

19. The method of claim 18, wherein the responsive optically sensible signals are useful for detecting muscular contraction and/or for measuring the resulting sarcomere changes.

20. The method of claim 13, wherein the needle is translated axially relative to the tissue, enabling multiple independent measurements from a single injection.

21. The method of claim 13, wherein the needle has differing optical properties for wide field or high resolution imaging.

22. The method of claim 13, further including:
using an engageable clamp-mechanism interface to attach the optical probe with an imaging-processing microscope while maintaining optical alignment for imaging processing of the biological tissue.

23. The method of claim 13, comprising:
providing a portable device for processing optical-signal data from the optical probe;
puncturing the tissue with the optical probe and needle; and
while in the tissue, collecting signals through the optical probe for high-resolution imaging of the tissue while lessening adverse image-quality degradation by controlling and maintaining power level and light-beam resolution for light pulsed through the light-delivering optical probe.

24. The method of claim 13, wherein the portable device is hand-held.

25. The method of claim 13, comprising:
puncturing the tissue with the optical probe and needle; and
while the optical probe is in the tissue, collecting signals for high-resolution imaging of the tissue while lessening adverse image-quality degradation by moving fluid near a biological-tissue image site for improving optical clarity.

26. The method of claim 25, wherein moving fluid includes removing blood from the biological-tissue image site.

27. The method of claim 25, wherein moving fluid includes providing saline to the biological-tissue image site.

28. The method of claim 25, further including using the optical probe to
send light pulses toward structure in the biological tissue at a sufficiently fast line-resolution rate to mitigate motion artifacts due to physiological motion,
cause, in response to the light pulses, signals to be generated from and across a sufficient portion of the structure to span the sarcomere length,
collect selected ones of the generated signals that are predominantly present due to properties intrinsic to the structure; and
providing data in response to the collected signals for high-resolution imaging of said portion of the tissue structure.

* * * * *

UNITED STATES PATENT AND TRADEMARK OFFICE
CERTIFICATE OF CORRECTION

PATENT NO.        : 8,897,858 B2  
APPLICATION NO.   : 13/305390  
DATED             : November 25, 2014  
INVENTOR(S)       : Sanchez et al.

Page 1 of 1

It is certified that error appears in the above-identified patent and that said Letters Patent is hereby corrected as shown below:

In the Claims

Col. 34, line 7, Claim 24: "claim 13" should read --claim 23--.

Signed and Sealed this
First Day of March, 2016

Michelle K. Lee
*Director of the United States Patent and Trademark Office*